(12) United States Patent
Steinmetz

(10) Patent No.: US 11,529,430 B2
(45) Date of Patent: Dec. 20, 2022

(54) POLYDOPAMINE DECORATED TOBACCO MOSAIC THERANOSTIC VIRUS NANOPARTICLES

(71) Applicant: CASE WESTERN RESERVE UNIVERSITY, Cleveland, OH (US)

(72) Inventor: Nicole F. Steinmetz, San Diego, CA (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 17/129,490

(22) Filed: Dec. 21, 2020

(65) Prior Publication Data

US 2021/0244831 A1 Aug. 12, 2021

Related U.S. Application Data

(60) Provisional application No. 62/951,129, filed on Dec. 20, 2019.

(51) Int. Cl.
| | | |
|---|---|---|
| *A61K 49/18* | (2006.01) | |
| *A61K 41/00* | (2020.01) | |
| *A61K 49/10* | (2006.01) | |

(52) U.S. Cl.
CPC ...... *A61K 49/1896* (2013.01); *A61K 41/0052* (2013.01); *A61K 49/108* (2013.01)

(58) Field of Classification Search
CPC .............. A61K 49/108; A61K 49/1896; A61K 41/0052
See application file for complete search history.

(56) References Cited

U.S. PATENT DOCUMENTS

| | | | |
|---|---|---|---|
| 9,925,281 B2 | 3/2018 | Steinme et al. | |
| 2015/0265729 A1* | 9/2015 | Steinmetz | A61K 49/1896 424/9.32 |

FOREIGN PATENT DOCUMENTS

| | | | | |
|---|---|---|---|---|
| CN | 105327354 A | * | 2/2016 | ............. A61K 47/02 |
| WO | 200118199 A1 | | 3/2001 | |

OTHER PUBLICATIONS

Hu et al., Nanoscale, 2019, 11, p. 9760-9768. (Year: 2019).*

Koudelka et al., Annu. Rev. Virol., 2015, 2, p. 379-401. (Year: 2015).*
Applicant: Case Western Reserve University; "Cancer Immunotherapy Using Virus Particles"; European Patent Application No. 18764856.3 for Supplementary European Search Report dated Dec. 22, 2020; 8 pgs.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Applicant: Case Western Reserve University; "Cancer Immunotherapy Using Virus Particles"; European Patent Application No. 21201960.8; Extended European Search Report dated Jan. 19, 2022; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Gonzalez Maria J et al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.
Patrick h. Iizotte: "Novel approaches to targeting innate immunity for cancer Immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Saunders K et al: "Efficient generation of cowpea mosaicvirus empty virus-like particles by the proteolytic processing of precursors in insect cells and plants", Virology, Elsevier, Amsterdam, NL, vol. 393, No. 2,Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].

* cited by examiner

*Primary Examiner* — Michael G. Hartley
*Assistant Examiner* — Leah H Schlientz
(74) *Attorney, Agent, or Firm* — Tarolli, Sundheim, Covell & Tummino LLP

(57) ABSTRACT

A nanoparticle for diagnostic, therapeutic, and/or theranostic applications includes a rod-shaped plant virus like particle (VLP), one or more gadolinium $T_1$ contrast agents conjugated to an interior surface of the VLP, and a layer of polydopamine (PDA) coated over a portion of the exterior surface of the VLP.

18 Claims, 14 Drawing Sheets

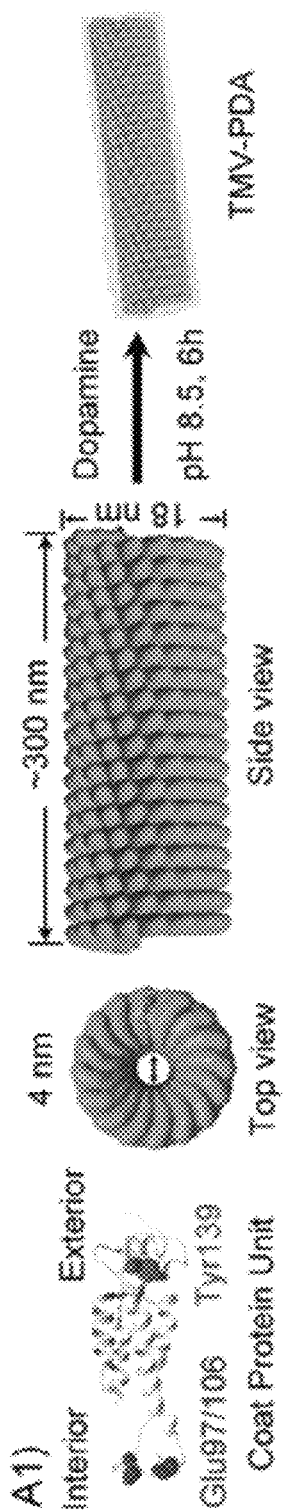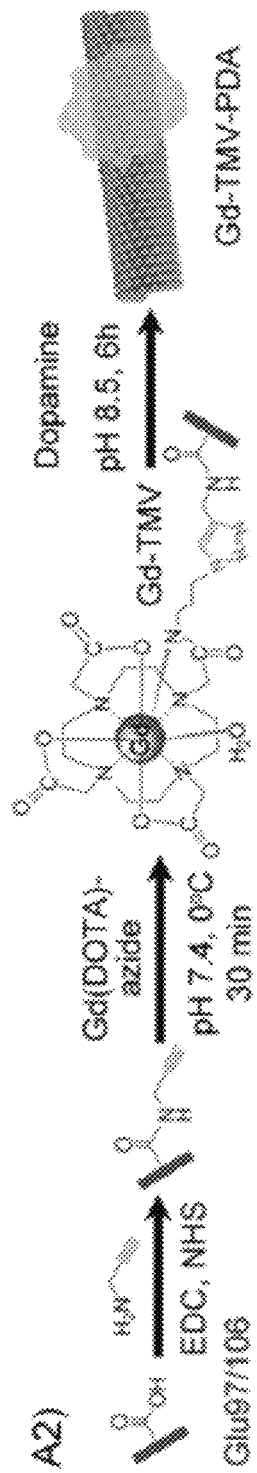
Fig. 1A1
Fig. 1A2

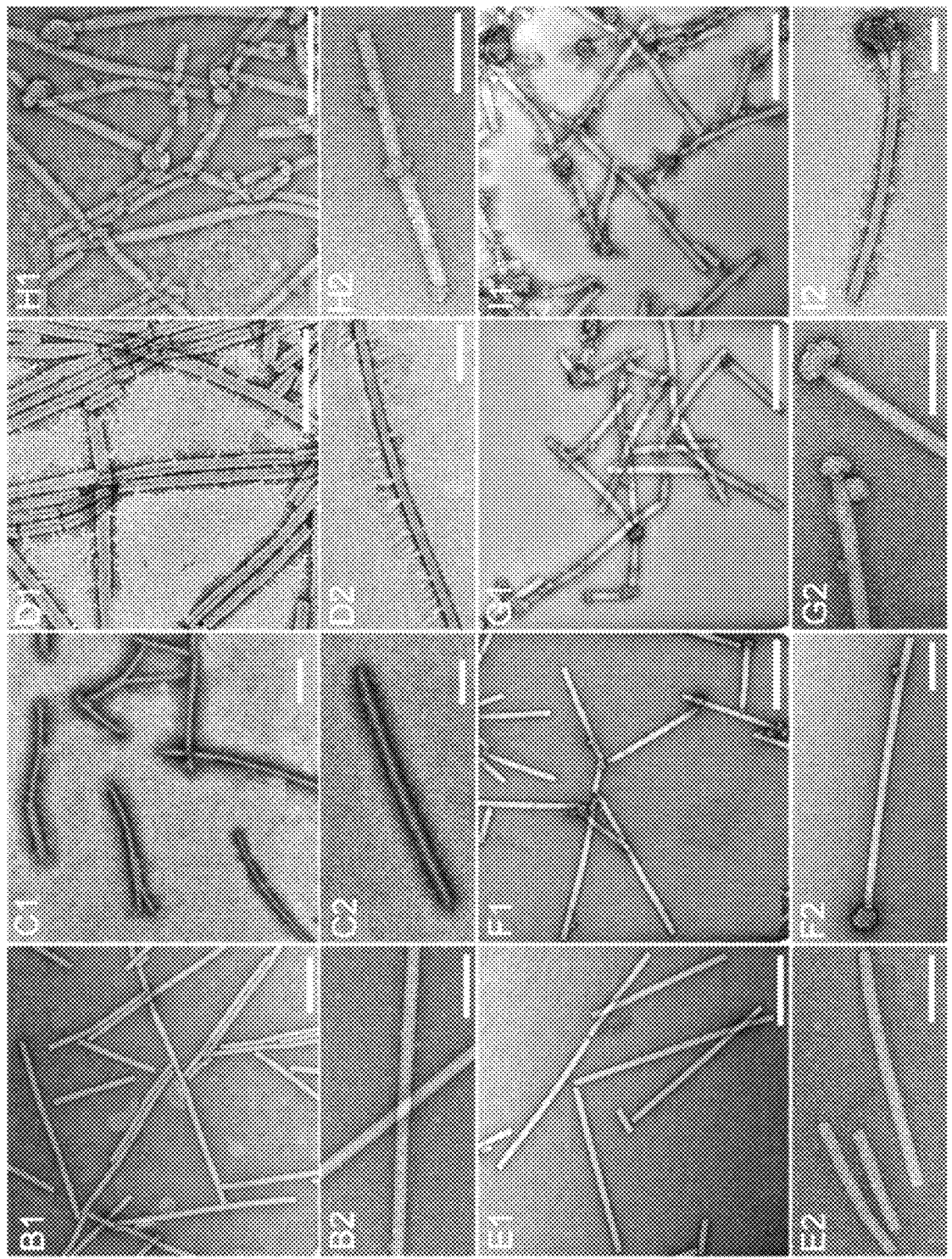
Fig. B1-I2

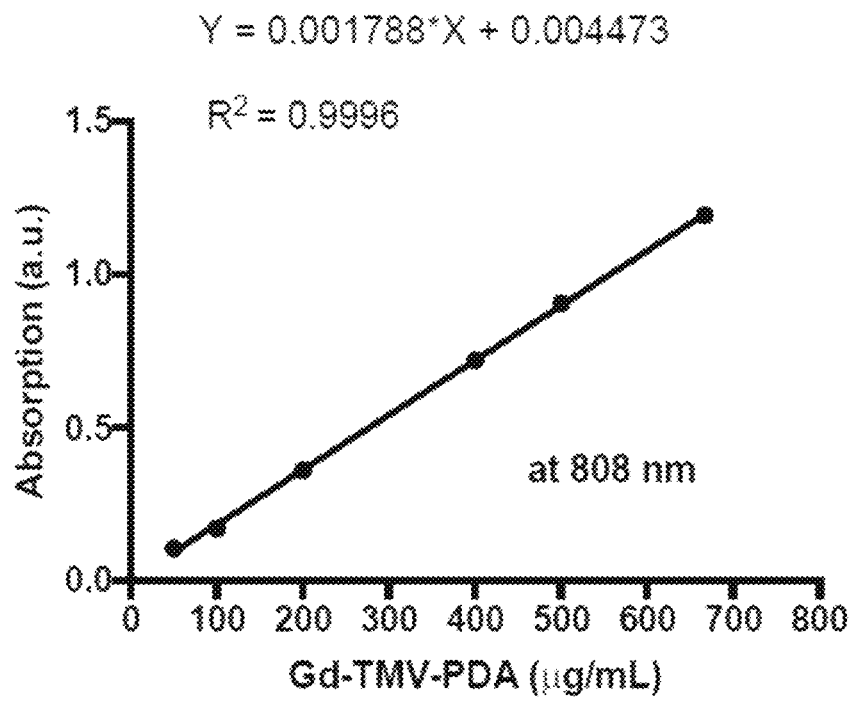
Fig. 7
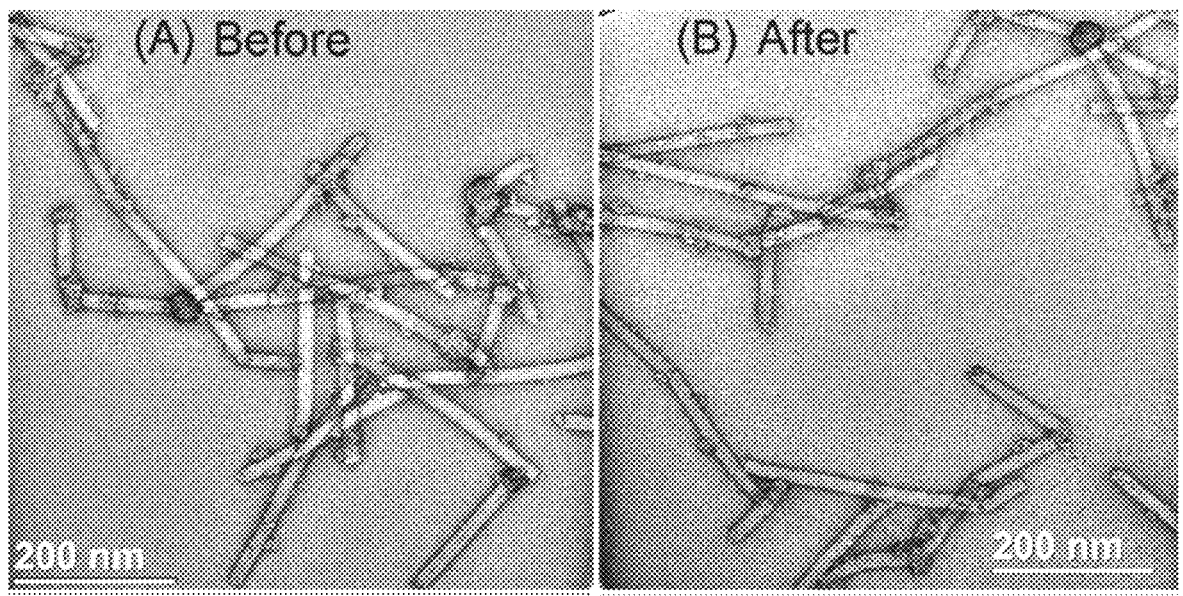
Fig. 8A
Fig. 8B

POLYDOPAMINE DECORATED TOBACCO MOSAIC THERANOSTIC VIRUS NANOPARTICLES

RELATED APPLICATION

This application claims priority from U.S. Provisional Application No. 62/951,129, filed Dec. 20, 2019, the subject matter of which is incorporated herein by reference in its entirety.

GOVERNMENT FUNDING

This invention was made with government support under Grant Nos. R01CA202814 awarded by The National Institutes of Health. The United States government has certain rights in the invention.

BACKGROUND

Nanocarrier platforms based on natural biological building blocks offer new opportunities in the biomedical and materials sciences. Viral nanoparticles (VNPs) are self-assembling supramolecular systems that can be used to develop bioinspired nanomaterials and nanocarriers due to their simple and inexpensive production, well-defined structural features, unique shapes and sizes, genetic programmability, and robust chemistries. VNPs based on plant viruses are particularly advantageous in medicine because they are biocompatible and biodegradable, but do not infect humans and other mammals. They can carry drugs, imaging agents, and other nanoparticles in their internal cavity by assembly, infusion, or internal surface modification, and the external surface can be chemically or genetically engineered to attach targeting ligands for tissue-specific delivery. Plant VNPs have already overcome many of the challenges of nanoparticle delivery, such as low stability in biological fluids, efficient delivery across membranes, avoidance of exocytosis, and targeting specificity. A broad range of plant VNPs have been established, such as those based on Cowpea mosaic virus (CPMV), Cowpea chlorotic mottle virus (CCMV), Brome mosaic virus (BMV), Potato virus X (PVX) and Tobacco mosaic virus (TMV).

Virus-like particles (VLPs) are a subset of VNPs, which lack the viral genome and assemble spontaneously from virus structural proteins into noninfectious protein cage-like structures. Many different virus structural proteins form VLPs when expressed in standard heterologous expression systems such as *Escherichia coli*, yeast, plants, mammalian cells, and insect cells. Such VLPs tend to be structurally and morphologically similar to the wildtype virus particles formed in vitro and demonstrate similar cell tropism, uptake, and intracellular trafficking.

SUMMARY

Embodiments described herein relate to nanoparticles that can be used in diagnostic, therapeutic, and/or theranostic applications. The nanoparticles include a rod-shaped virus-like particle (VLP), one or more gadolinium contrast agents conjugated to an interior surface of the VLP, and a layer of polydopamine (PDA) coated over a portion of the exterior surface of the VLP. The rod-shaped VLP can belong to the Virgaviridae family, such as the tobacco mosaic virus (TMV) species.

In some embodiments, the one or more gadolinium contrast agents can include a chelated gadolinium contrast agent, such as gadolinium-DOTA (Gd-DOTA). The one or more gadolinium contrast agents can be directly conjugated to the rod-shaped plant VLP. In some aspects, the one or more gadolinium $T_1$ contrast agents can be linked to the rod-shaped plant VLPs via a linker.

In other embodiments, the nanoparticle PDA layer is prepared by in situ self-polymerization of dopamine on the VLP. The weight ratio of the VLP conjugated with the gadolinium $T_1$ contrast agents to polydopamine is about 1:1 to about 1:2.

In some embodiments, the nanoparticles can be used in a method of detecting cancer in a subject. The method includes administering to the subject a plurality of the nanoparticles. The method also includes detecting the nanoparticles in the subject using one or more imaging devices subsequent to administering the nanoparticles to determine the location and/or distribution of the cancer in the subject.

In some embodiments, the detected cancer can include breast cancer or prostate cancer.

In other embodiments, the one or more imaging devices can be selected from the group consisting of a magnetic resonance imaging (MRI) modality and a photoacoustic (PA) imaging modality.

Other embodiments described herein relate to a method of treating cancer in a subject in need thereof. The method includes administering to the subject a therapeutically effective amount of a plurality of the nanoparticles.

In some embodiments, the method also includes detecting the nanoparticles in the subject using one or more imaging devices subsequent to administering the nanoparticles to determine the location and/or distribution of the cancer in the subject.

The method can further include delivering photothermal therapy (PTT) to the detected VLPs at the determined location of the cancer in the subject.

In some embodiments, the PTT can include the use of a device that emits electromagnetic radiation such that at least a portion of cancer cells in the detected cancer are damaged or killed. The electromagnetic radiation can include near-infrared radiation (NIR) delivered by laser. The one or more imaging devices can be selected from the group consisting of a magnetic resonance imaging (MRI) modality and a photoacoustic (PA) imaging modality.

BRIEF DESCRIPTION OF THE DRAWINGS

FIGS. 1(A1-I2) illustrate images of the (A1) Structure and Tobacco Mosaic Virus (TMV) coat protein, showing the surface-exposed internal glutamic acid and external tyrosine residues, and the structure of the assembled wild-type capsid coated with polydopamine (TMV-PDA). (A2) Strategy for internal loading of Gd-DOTA (Gd-TMV) and partial decoration with PDA (Gd-TMV-PDA). Images created using UCSF Chimera software, PDB entry 2TMV and ChemDraw v15.0; and transmission electron micrographs (TEM) showing B1-2 native wild-type TMV and TMV-PDA with different reaction mass ratios of TMV:dopamine: (C1-2) 2:2.5 and (d1-2) 2:3.5. TEM of (E1-2) Gd-TMV and Gd-TMV-PDA with different mass ratios of Gd-TMV: dopamine: (F1-2) 2:2.5, (G1-2) 2:3.5, (H1-2)2:5, and (I1-2) 2:7. Scale bar=200 nm (B1 -I1) and 100 nm (B2-I2).

FIG. 7 illustrates the absorption at 808 nm of different concentrations of Gd-TMV-PDA in PBS buffer pH 7.4

DETAILED DESCRIPTION

Figure 2A:
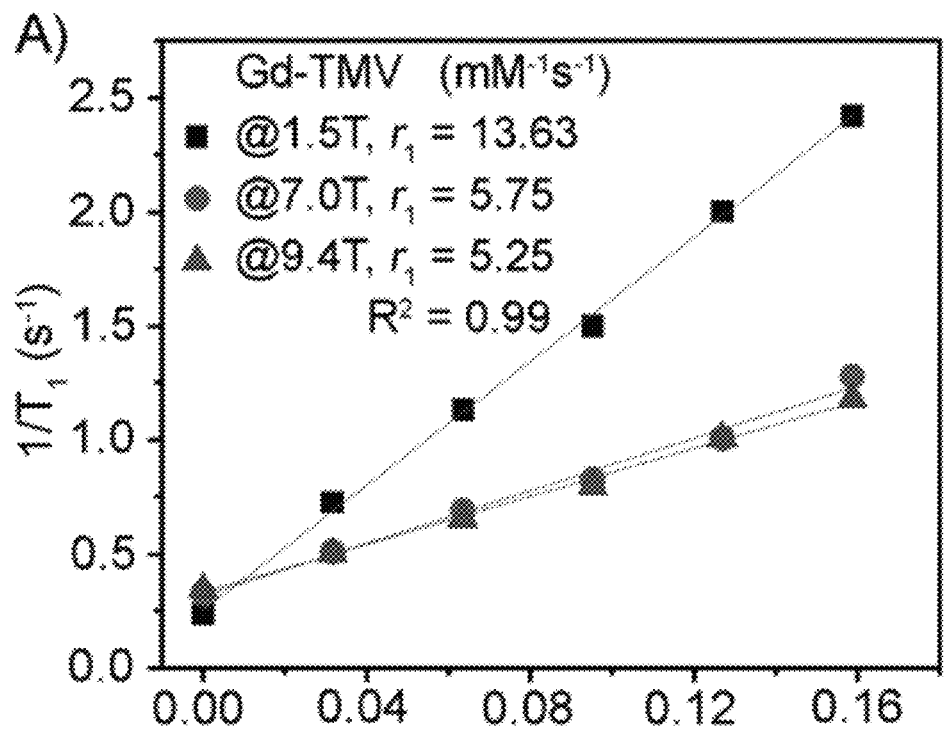
FIGS. 2(A-F) illustrate graphs and phantom maps showing the water proton longitudinal ($r_1$) relaxation of (A) Gd-TMV and (B) Gd-TMV-PDA as a function of $Gd^{3+}$ concentration measured at 37° C. in magnetic fields of 1.5, 7.0 and 9.4 T. The $T_1$ mapping phantoms of (C) Gd-TMV and (D) Gd-TMV-PDA in aqueous solutions at various concentrations of Gd3+ in magnetic fields of 7.0 and 9.4 T. (E) The $r_1$ nuclear magnetic relaxation dispersion (NMRD) profiles (0.01-70 MHz) were obtained for the aqueous suspensions of Gd-TMV (■) and Gd-TMV-PDA (●) at 25° C. normalized to 1 mM Gd3+. (F) The in vitro $T_1$-mapping of PC-3 cells taking up different concentrations of Gd-TMV-PDA at 37° C. for 3 h. Corresponding quantities of $Gd^{3+}$ taken up by PC-3 cells were determined by ICP-OES and the Bradford protein assay following MRI.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The terminology used in the description of the invention herein is for describing particular embodiments only and is not intended to be limiting of the invention. All publications, patent applications, patents, and other references mentioned herein are incorporated by reference in their entirety.

As used in this specification and the appended claims, the singular forms "a", "an" and "the" include plural references unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of +20% or 110%, more preferably ±5%, even more preferably ±1%, and still more preferably ±0.1% from the specified value, as such variations are appropriate to perform the disclosed methods.

"Image" or "imaging" refers to a procedure that produces a picture of an area of the body, for example, a region, organs, bones, tissues, cells or blood.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

"Prevention" or "preventing", as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or because of family history.

A "subject," as used herein, can be any animal, and may be referred to as the patient. Preferably, the subject is a vertebrate animal, and more preferably, the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

As used herein, the term "relaxation time" refers to the time required for a nucleus that has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and T2. $T_1$ is referred to as the longitudinal relaxation time and T2 is referred to as the transverse relaxation time. As used herein, the term "relaxation time" refers to the above-described relaxation times either together or in the alternative. As used herein, the term "relaxivity" refers to how an MRI contrast agent reflects how the relaxation rates of a solution change as a function of concentration [C]. Since a contrast agent may affect the two relaxation rates (1/T1 and 1/T2) individually, there are two corresponding relaxivities, denoted $r_1$ and r2. An exhaustive treatise on nuclear relaxation is available in Banci, L, et al. Nuclear and Electron Relaxation, VCH, Weinheim, 1991, which is herein incorporated by reference.

The terms "therapeutically effective" and "pharmacologically effective" are intended to qualify the amount of each agent, which will achieve the goal of decreasing disease severity while avoiding adverse side effects such as those typically associated with alternative therapies. The therapeutically effective amount may be administered in one or more doses.

"Targeting," as used herein, refers to the ability of modified virus-like particles to be delivered to, and preferentially accumulate in, cancer tissue in a subject compared to normal tissue.

As used herein, the term "diagnostically effective amount" refers to an amount of contrast agent that is sufficient to enable imaging of the contrast agent in cells, tissues, or organisms using imaging equipment.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host.

Embodiments described relate to polydopamine (PDA) coated virus-like particles (VLPs) derived from rod-shaped plant viruses, such as tobacco mosaic virus (TMV) that are conjugated to one or more gadolinium contrast agents. The PDA coated nanoparticles allow for the simultaneous use of multi-modal imaging diagnostics and photothermal therapy (PTT) for targeting, detecting and/or the treatment of cancer in a subject.

In some embodiments, the nanoparticles include a rod-shaped virus-like particle (VLP), one or more gadolinium $T_1$ contrast agents conjugated to an interior surface of the VLP, and a layer of polydopamine (PDA) coated over a portion of the exterior surface of the VLP. The rod-shaped VLP can belong to the Virgaviridae family, such as the tobacco mosaic virus (TMV) species.

A rod-shaped plant virus is a virus that primarily infects plants, is non-enveloped, and is shaped as a rigid helical rod with a helical symmetry. Rod-shaped viruses also include a central canal. Rod-shaped plant virus particles are distinguished from filamentous plant virus particles as a result of being inflexible, shorter, and thicker in diameter.

In some embodiments, the rod-shaped plant virus belongs to a specific virus family, genus, or species. For example, in some embodiments, the rod-shaped plant virus belongs to the Virgaviridae family. Virus from the family Virgaviridae have a length of about 200 to about 400 nm, and a diameter of about 15-25 nm. Virgaviridae have other characteristics, such as having a single-stranded RNA positive sense genome with a 3'-tRNA like structure, no polyA tail, and coat proteins of 19-24 kilodaltons. The Virgaviridae family includes the genus *Furovirus, Hordevirus, Pecluvirus, Pomovirus, Tobamovirus*, and *Tobravirus.*

Some embodiments relate to PDA coated Tobamovirus virus-like particles (VLPs) where the Tobamovirus VLPs are derived from a virus of the Tobamovirus genus.

The diameter of a Tobamovirus is about 18 nm. Use of a Tobamovirus VLP as described herein provides the advantages of improved physical stability (e.g., after cargo loading as well as in storage) and production consistency.

A Tobamovirus virus can be selected from a group consisting of Bell pepper mottle virus, Brugmansia mild mottle virus, Cactus mild mottle virus, Clitoria yellow mottle virus, Cucumber fruit mottle mosaic virus, Cucumber green mottle mosaic virus, Cucumber mottle virus, Frangipani mosaic virus, Hibiscus latent Fort Pierce virus, Hibiscus latent Singapore virus, Kyuri green mottle mosaic virus, Maracuja mosaic virus, Obuda pepper virus, Odontoglossum ringspot virus, Opuntia chlorotic ringspot virus, Paprika mild mottle virus, Passion fruit mosaic virus, Pepper mild mottle virus, Plumeria mosaic virus, Rattail cactus necrosis-associated virus, Rehmannia mosaic virus, Ribgrass mosaic virus, Streptocarpus flower break virus, Sunn-hemp mosaic virus, Tobacco latent virus, Tobacco mild green mosaic virus, Tobacco mosaic virus, Tomato brown rugose fruit virus, Tomato mosaic virus, Tomato mottle mosaic virus, Tropical soda apple mosaic virus, Turnip vein-clearing virus, Ullucus mild mottle virus, Wasabi mottle virus, Yellow tailflower mild mottle virus, Youcai mosaic virus, and Zucchini green mottle mosaic virus.

In certain embodiments, the rod-shaped plant Tobamovirus VLP can be derived from the tobacco mosaic virus (TMV) species. TMV has a capsid made from 2130 molecules of coat protein and one molecule of positive-sense genomic single strand RNA 6400 bases long. The coat protein self-assembles into the rod like helical structure (16.3 proteins per helix turn) around the RNA, which forms a hairpin loop structure. The protein monomer consists of 158 amino acids, which are assembled into four main alpha-helices, which are joined by a prominent loop proximal to the axis of the virion. TMV virions are ~300 nm in length and ~18 nm in diameter. Negatively stained electron microphotographs show a distinct inner channel of ~4 nm.

The coat protein of a Tobamovirus, such as TMV, for use as a PDA coated VLP described herein, can be synthetically produced using methods well known in the art. Methods of producing Tobamovirus VLPs can include the steps of: (a) producing a recombinant polynucleotide sequence, (b) constructing a recombinant vector comprising a regulatory sequence and the recombinant polynucleotide sequence of step (a), (c) transforming a host cell with the recombinant vector of step (b) to produce a recombinant host cell, (d) growing the recombinant host cell of step (c) to produce Tobamovirus VLPs, and (e) purifying the Tobamovirus VLPs of step (d). The recombinant vector can further include a regulatory sequence. Exemplary regulatory sequence can include T7, SP6 and T3 promoters.

In an exemplary embodiment, Tobamovirus-derived VLPs can be formed from Tobamovirus structural proteins encoded by a recombinant polynucleotide sequence that are expressed in an *Escherichia coli*, yeast or baculovirus heterologous expression system. In some embodiments, the heterologous expression system is an *E. coli* expression system. The *E. coli* strain can be selected from the group consisting of JM101, DH5a, BL21, HB101, BL21(DE3) pLys S, XL-1 Blue and Rossetta. In some embodiments, the recombinant polynucleotide sequence can include, for example, a nucleotide sequence encoding all, or a truncated portion, of the Tobamovirus coat protein.

In some embodiments, the rod-shaped VLPs are loaded with or conjugated to one or more gadolinium contrast agents. The gadolinium contrast agent can be a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Contrast agents are used to enhance the differentiation between tissue regions in order to better image the tissue.

In some embodiments, the one or more gadolinium contrast agents can include a macrocylic gadolinium complex, such as a gadolinium (III) macrocycle complex. The Gd(III) macrocycle complex conjugated to the VLP can include a chelating compound to reduce the longitudinal relaxation time of nearby water protons, aided by the high magnetic moment and symmetrical S state of the Gd(III) ion. A number of chelating compounds have been developed to increase the coordinated water molecules for lanthanide, ions such as gadolinium, which can almost double the relaxivity rate. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA). See Gugliotta et al., Org. Biomol. Chem., 8, 4569 (2010), the disclosure of which is incorporated herein by reference. In certain embodiments, the gadolinium chelating molecule for use in a Gd(III) macrocycle complex described herein includes DOTA, such as gadolinium-DOTA (Gd-DOTA).

The rod-shaped VLPs described herein may be engineered and tailored for desired imaging applications through multiple approaches, such as genetic modification, non-covalent infusion and/or bioconjugate chemistry. For example, protein engineering can be used to introduce imaging functionalities, at the internal interface of VLPs.

The term "conjugating" when made in reference to one or more gadolinium contrast agents and a rod-shaped plant VLP as used herein means covalently linking the one or more gadolinium contrast agents to the rod-shaped plant VLP. In certain embodiments, the nature and size of the one or more gadolinium contrast agents and the site at which it is covalently linked to the VLP do not interfere with the biodistribution of the modified virus and/or interfere with the internalization of the rod-shaped plant VLPs by cancer cells.

Because viral capsids are proteinaceous, standard bioconjugation protocols that address chemically reactive amino acid side chains can be used as with other proteins. The most common reactions used to modify viruses involve the reactive side chains of lysine, cysteine and aspartic/glutamic acid residues, which are accessible to N-hydroxysuccinimidyl (NHS) chemistry, Michael addition to maleimides, and carbodiimide activation, respectively.

The one or more gadolinium contrast agents can be conjugated to a rod-shaped plant VLP either directly or indirectly (e.g., via a linker group). In some embodiments, the one or more gadolinium contrast agents can be directly attached to a functional group capable of reacting with the agent. For example, TMV includes an internal surface glutamic acid residue (GLU97/106) that can be functionalized using a well-established copper-catalyzed azide-alkyne cycloaddition (CuAAC) strategy also known as click chemistry and then conjugated with a macrocyclic $T_1$-MRI contrast agent Gd-DOTA-azide (see FIG. 1A1). The carboxylate groups of glutamic acid residues can be targeted for functionalization using carbodiimide activated linker molecules. In addition, genetic modification can be applied to introduce any desired functional residue, including non-natural amino acids, e.g., alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the imaging agent or the virus particle, and thus increase the coupling efficiency. Suitable linkage chemistries include maleimidyl linkers and alkyl halide linkers and succinimidyl (e.g., N-hydroxysuccinimidyl (NHS)) linkers (which react with a primary amine on the plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, 111.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to Na104-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2: 148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

Bifunctional chelating agents including N-hydroxysuccinimide/isothiocyanates, amine, maleimide, and azide chemical linkers can be used for conjugation to amines, carboxylatic acids, thiols, and alkynes.

In other embodiments, the rod-shaped plant VLPs can be loaded with one or more gadolinium $T_1$ contrast agents using non-covalent infusion techniques that facilitate efficient cargo loading of one or more imaging agents into the virus or VLPs. For example, to non-covalently infuse one or more gadolinium contrast agents rod-shaped VLPs described herein the VLPs can be incubated in a bathing solution containing one or more gadolinium contrast agents at a molar excesses ranging from about 100 to about 10,000 molecules per VLP) in KP buffer with 10% (v/v) DMSO overnight at room temperature. After the reaction, excess guest molecules can be removed by ultracentrifugation and the amount of protein and cargo can be quantified by the Bradford assay and UV/visible spectroscopy, respectively.

The number of gadolinium contrast agents that can be loaded onto the virus particle depends on the number of attachment sites available and the chemistries employed to link the gadolinium contrast agents to the virus particle. In some embodiments, each virus particle is loaded with about 1 to at least about 5000 gadolinium contrast agents.

In some embodiments, a biocompatible PDA material can be used to coat a portion of the exterior surface of the rod-shaped plant VLP nanoparticles described herein. PDA is a melanin-like mimic of mussel adhesion proteins, exhibiting excellent photothermal stability, biocompatibility and biodegradability. It was found using TEM analysis that the PDA coated rod-shaped plant virus VLPs conjugated with the one or more gadolinium $T_1$ contrast agents to the internal surface via a click reaction maintain the shape and morphology of a wild-type particle (see FIG. 1B). It was also found that the PDA coating display on a rod-shaped plant VLP loaded with a contrast agent significantly increased the longitudinal relaxivity (i.e., $r_1$-relaxivity) of the contrast agent (see FIG. 2B). It was further found that the PDA coated VLPs loaded with a contrast agent achieved strong near-infrared absorption with high photothermal conversion efficiency (see FIGS. 3A-F) as well as excellent photoacoustic imaging properties (See FIGS. 4A-B).

PDA for coating the surface of the rod-shaped plant VLPs described herein can be produced by the self-polymerization of dopamine in a mild reaction environment. In one example, 2 mg of a tobacco mosaic virus-like particle loaded with a gadolinium (Gd) contrast agent can be coated with PDA by in situ self-polymerization using dopamine at a dose range of about 2.5 mg to about 7 mg. It was found that increasing the dopamine dose from 2.5 mg to 7 mg caused significant changes to the PDA coating on the Gd-TMV particle surface, with knot-like protrusions 10-40 nm in depth forming at dopamine doses of 2.5, 3.5 and 5 mg but both a full coating and knots at the highest dose of 7 mg. It was also shown that PDA coated TMV loaded with Gd having consistent morphology can be prepared using a dose of about 2.5 to about 3.5 mg dopamine. Therefore, in some embodiments, PDA coated rod-shaped plant VLPs loaded with the Gd contrast agent can be prepared using about 2 mg of the Gd conjugated VLPs and about 2.5 to about 3.5 mg dopamine. In other embodiments, the weight ratio of the VLP conjugated with the gadolinium contrast agents to polydopamine can be about 1:1 to about 1:2. In a particular embodiment, PDA coated rod-shaped plant VLPs loaded with Gd contrast agent, can be prepared using a dose of about 3.5 mg dopamine and about 2 mg Gd conjugated VLPs.

In some embodiments, PDA covers just a portion of the exterior surface of the rod-shaped plant virus particle and not the entire exterior surface of the rod-shaped plant virus particle, or it may cover a substantial portion of the exterior of the plant virus particle. For example, the biocompatible PDA coating may cover at least about 10%, 20, 30%, 40% 50%, 60%, 70%, 80%, or at least about 90% of the surface of the exterior of the virus particle but less than 100% of the exterior surface of the rod-shaped plant virus particle. In other embodiments, the amount of PDA applied to the rod-shaped plant virus particle is an amount effective to cover just the ends of the rod-shaped plant virus particle Once the portion of the exterior surface of Gd conjugated rod-shaped plant VLP is covered with PDA, the Gd-PDA coated nanoparticles can be characterized using numerous modalities, such as by ultra-high field MRI, confocal laser scanning microscopy, transmission electron microscopy (TEM), near infrared (NIR) camera, photoacoustic analysis, and their cytotoxic efficacy can been evaluated in human normal, and cancer cell lines (e.g., breast and prostate cancer cell).

Plant virus particles, such as rod-shaped plant VLPs have been shown to preferentially accumulate in diseased tissue, such as cancer tissue or inflamed tissue (e.g., atherosclerotic blood vessels). While not intending to be bound by theory, it appears that plant virus particles (e.g., rod-shaped plant virus particles) are taken up by blood components such as macrophage cells of the immune system, which subsequently accumulate in diseased tissue (e.g., a tumor), thereby targeting delivery of the plant VLPs to cells at the disease site.

Therefore, in some embodiments, the PDA coated rod-shaped plant VLPs conjugated to, or loaded with, gadolinium contrast agents, can be used in a method to target diseased tissue in a subject. In certain embodiments, the diseased tissue is cancer tissue. The method includes administering a plurality of PDA coated rod-shaped plant VLPs loaded with or conjugated to one or more gadolinium contrast agents to the subject. As defined herein, targeting diseased tissue refers to the ability of the PDA coated rod-shaped plant VLPs to reach and preferably accumulate within diseased tissue after being administered to the subject. The ability of PDA coated rod-shaped plant VLPs to target diseased tissue, such as cancer tissue, is supported by the characterization, and cytotoxicity studies described herein.

While not intending to be bound by theory, it is believed that the PDA coated rod-shaped plant VLPs are preferentially internalized by cancer cells over non-cancerous cells via endocytosis, thereby delivering the functionalized VLPs to the tumor cells at a much higher efficiency than non-transformed cells. Nanoparticles described herein can deliver and internalize about 10%, about 20%, about 30%, about 40%, about 50%, about 60%, about 70%, about 80%, about 90% or even about 100% of administered nanoparticles to a subject's cancer cells. In specific embodiments, the PDA coated VLPs described herein can deliver and internalize about 50% to about 100% of administered PDA coated rod-shaped plant VLPs conjugated to, or loaded with, contrast agents to cancer cells.

Once PDA coated rod-shaped plant VLPs conjugated to, or loaded with, gadolinium $T_1$ contrast agents, have been administered to a subject in order to target diseased tissue, an image of the targeted diseased tissue region can be generated. Therefore, in some embodiments, methods described herein can further include the step of imaging the cancer tissue in the subject using one or more imaging devices wherein the cancer tissue is imaged subsequent to administering PDA coated rod-shaped VLPs conjugated to, or loaded with, one or more gadolinium $T_1$ contrast agents.

In one example, a diagnostically effective amount of PDA coated rod-shaped plant VLPs conjugated to, or loaded with one or more gadolinium contrast agents can be administered to a subject, and an image of the tissue region of the subject to which the VLPs have been distributed/targeted (e.g., cancer tissue) is then generated. The PDA coated rod-shaped plant VLPs can include any of the specific features described herein.

In certain embodiments, the diseased tissue imaged is cancer tissue. For example, the cancer tissue can include a tumor. A tumor is an abnormal mass of tissue as a result of abnormal growth or division of cells caused by cancer. Tumors can occur in a variety of different types of tissue such as the breast, lung, brain, liver kidney, colon, and prostate, can be malignant or benign, and generally vary in size from about 1 cm to about 5 cm.

In order to generate an image of the tissue region, it is necessary for an effective amount of gadolinium contrast agent to reach the tissue region of interest, but it is not necessary that the gadolinium contrast agent be localized in this region alone. However, in some embodiments, the nanoparticles are targeted or administered locally such that they are present primarily in the tissue region of interest. Examples of images include two-dimensional cross-sectional views and three dimensional images. In some embodiments, a computer is used to analyze the data generated by the gadolinium contrast agents in order to generate a visual image. The tissue region can be an organ of a subject such as the heart, lungs, or blood vessels. In other embodiments, the tissue region can be diseased tissue, or tissue that is suspected of being diseased, such as a tumor or atherosclerotic tissue.

In certain embodiments, imaging methods include magnetic resonance imaging (MRI), photoacoustic (PA) imaging, computed tomography, and positive emission tomography.

In particular embodiments, the PDA coated rod-shaped plant VLPs conjugated to, or loaded with one or more gadolinium contrast agents are imaged in a subject using an MRI imaging method. MRI provides a good contrast between the different soft tissues of the body, which makes it especially useful in imaging the brain, muscles, the heart, and cancers compared with other medical imaging techniques such as computed tomography or X-rays. An MRI scanner is a device in which the subject lies within a large, powerful magnet where the magnetic field is used to align the magnetization of some atomic nuclei in the body, and radio frequency magnetic fields are applied to systematically alter the alignment of this magnetization. This causes the nuclei to produce a rotating magnetic field detectable by the scanner and this information is recorded to construct an image of a tissue region. Magnetic field gradients cause nuclei at different locations to process at different speeds, allowing spatial information to be recovered using Fourier analysis of the measured signal. By using gradients in different directions, 2D images or 3D volumes can be obtained in any arbitrary orientation.

Various different types of MRI scans can be conducted, including T1-weighted MRI, T2-weighted MRI, and spin density weighted MRI. In some embodiments, the PDA coated rod-shaped plant VLPs of the invention are conjugated to, or loaded with, gadolinium $T_1$ contrast agents to facilitate a T1-weighted MRI scan. T1-weighted scans refer to a set of standard scans that depict differences in the spin-lattice (or T1) relaxation time of various tissues within the body. T1 weighted images can be acquired using either spin echo or gradient-echo sequences. T1-weighted contrast can be increased with the application of an inversion recovery RF pulse. Gradient-echo based T1-weighted sequences can be acquired very rapidly because of their ability to use short inter-pulse repetition times (TR).

In some embodiments, the PDA coated rod-shaped plant VLPs administered to a subject can be imaged using photoacoustic (PA) imaging. PA imaging is based on the photo acoustic effect, which relies on the detection of acoustic waves generated by biological targets following the absorption of light. In certain embodiments, PA imaging includes multispectral optoacoustic tomography (MSOT).

Additional imaging methods can include the use of Computed tomography (CT) and Positive emission tomograph (PET). CT refers to a diagnostic imaging tool that computes multiple x-ray cross sections to produce a cross-sectional view of the vascular system, organs, bones, and tissues. PET refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer.

By PDA coating the rod-shaped plant VLPs conjugated to, or loaded with, contrast agents, several imaging strategies (i.e., multi-modal imaging) as well as a cytotoxic therapeutic strategy e.g., PTT) can be simultaneously implemented. In particular embodiments, multi-modal imaging can include dual modal imaging employing a combination of MRI and PA to image the disease (e.g., cancer) tissue in the subject. For example, dual-modal imaging of cancer tissue in a subject can include using a combination of ultrahigh-field MRI (UHFMRI) and multispectral optoacoustic tomography (MSOT).

Thus, in some embodiments, a plurality of PDA coated rod-shaped plant VLPs loaded with a gadolinium contrast agent, such as Gd-DOTA, can be employed as a theranostic contrasting agent for several individual visualization techniques, or for multimodal imaging useful for guided photothermal therapy. For example, it is shown that Gd-loaded PDA coated TMV VLPs allow the localization of cancer cells by MRI and PA and further allow targeted killing by irradiation with a laser using PTT. In other embodiments, the PDA coated the rod-shaped plant VLPs conjugated to, or loaded with, a gadolinium contrast agent, are used only for imaging strategies, such as MRI contrast agents and/or PA agents, with or without subsequent photothermal therapy.

Photothermal therapy (PTT) refers to efforts to use electromagnetic radiation (most often in infrared wavelengths) for the treatment of various medical conditions, including cancer. This approach is an extension of photodynamic therapy, in which a photosensitizer is excited with specific band light. This activation brings the sensitizer to an excited state where it then releases vibrational energy (heat), which is what kills the targeted cells. Unlike photodynamic therapy, PTT does not require oxygen to interact with the target cells or tissues.

Thus, in certain embodiments, the PDA coated rod-shaped plant VLPs conjugated to, or loaded with, gadolinium contrast agents described herein are used as theranostic nanoparticles for treating cancer in a subject. It is contemplated that the PDA coated rod-shaped plant VLPs conjugated to, or loaded with, gadolinium contrast agents are targeted to cancer cells, tissue or other site of interest associated with the cancer, and in the course of PTT will absorb near infrared (NIR) radiation delivered thereto and, upon becoming heated by the NIR, result in selective thermolysis or ablation or other damage or cell death without damaging untargeted cells or tissues. In some embodiments, the photothermal therapy causes the cell death or damage to at least 10% (e.g., at least 10%, 20%, 30%, 40%, 50%, 60%, 70%, 80%, 90%, or 99%) of the targeted cancer cells in a subject.

Devices and methods for delivering radiation of a particular wavelength, such as by, but not limited to, lasers, to a targeted site are well-known and standard in the art. Exemplary devices for administering or delivering PTT can include a near infrared (NIR) laser or other NIR emitting device, and a visible light source that emits visible light, wherein the visible light source is positioned with respect to the NIR laser such that the visible light indicates where the NIR laser is shining on a subject. In certain embodiments, the device emits electromagnetic radiation with a wavelength between about 800 nm and 1000 nm. In other embodiments, the device emits electromagnetic radiation with a wavelength between about 650 nm and 1000 nm Due in part to their preferential uptake/internalization by cancer cells over noncancerous cells, PDA coated rod-shaped plant VLPs loaded with or conjugated to one or more gadolinium contrast agents can be used to detect and/or treat a variety of different types of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features.

A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers detected and/or treated using PDA coated VLPs in a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B.

Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). In certain embodiments, the PDA coated rod-shaped plant VLPs are used to detect and/or treat breast or prostate cancer tissue.

In some embodiments, a plurality of PDA coated rod-shaped plant VLPs conjugated to, or loaded with, one or more gadolinium contrast agents are administered together with a pharmaceutically acceptable carrier to provide a pharmaceutical formulation. Pharmaceutically acceptable carriers enable the PDA coated rod-shaped plant VLPs to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulf oxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the PDA coated rod-shaped plant VLPs into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated PDA coated rod-shaped plant VLPs conjugated to, or loaded with, gadolinium contrast agents can be administered as a single dose or in multiple doses.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the PDA coated rod-shaped plant VLPs conjugated to, or loaded with, gadolinium $T_1$ contrast agents vary depending upon many different factors, including means of administration, particular imaging agents used, target site, physiological state of the patient, whether the patient is human or an animal, other medications administered, and whether treatment is prophylactic or therapeutic.

The dosage of an imaging agent included in a plurality of PDA coated rod-shaped plant VLPs for administration to a mammalian subject or an avian subject in accordance with a method described herein ranges from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg.

A suitable amount of PDA coated rod-shaped plant VLPs are used to provide the desired dosage of agent(s).

An example of a detection or treatment regime typically entails administration prior to the use of one or more imaging modalities and a PTT modality (e.g., 808 nm laser) on the subject. The plurality of PDA coated rod-shaped plant VLPs can be administered on multiple occasions. Alternatively, the PDA coated rod-shaped plant VLPs can be administered as a sustained release formulation, in which case less frequent administration is required. In therapeutic applications, a relatively high dosage at relatively short intervals is sometimes required until progression of the disease is reduced or terminated, and preferably, until the subject shows partial or complete amelioration of symptoms of disease. Thereafter, the patient subject can be administered a prophylactic regime.

Compositions including PDA coated rod-shaped plant VLPs conjugated to, or loaded with, gadolinium $T_1$ contrast agents described herein can also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized SEPHAROSE, agarose, cellulose, and the like), polymeric amino acids, amino acid copolymers, and lipid aggregates (such as oil droplets or liposomes).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The present invention is illustrated by the following example. It is to be understood that the particular example, materials, amounts, and procedures are to be interpreted broadly in accordance with the scope and spirit of the invention as set forth herein.

Example

Multimodal image-guided therapy is a promising strategy to pinpoint lesion sites, facilitate drug delivery, and monitor therapeutic responses. A nanotheranostic (one-for-all) agent combines multimodal imaging with the delivery of drugs, immunomodulators, gene vectors, or photothermal/photodynamic reagents in a single formulation. Various imaging modalities can be used, including magnetic resonance imaging (MRI) and photoacoustic (PA) imaging.

There are several challenges that must be addressed before these goals are achieved. For example, MRI suffers from relatively low sensitivity. Various of MRI contrast agents have been developed to alter the longitudinal (T1) or transverse (T2) relaxation times of the surrounding water protons thus increasing the contrast between target lesions and the background to improve the sensitivity of MRI for clinical diagnosis. Gadolinium(III) ions (Gd3+) in chelator complexes such as DOTA (monoamide-1,4,7,10-tetraazacyclododecane-N—N'—N"—N'"-tetraacetic acid) form suitable contrast agents that shorten T1 in low-strength magnetic fields (≤1.5 T), which are used in more than 30% of clinical MRI scans. However, these Gdbased contrast agents suffer from poor longitudinal relaxivity (r1), which rapidly decreases with increasing field strength and thus limits their effectiveness during MRI. Research has therefore focused on the development of contrast agents with high r1-relaxivity, which are compatible with higher-field-strength MRI scanners.

We therefore hypothesized that the combination of PDA and Gd-loaded TMV would be an ideal platform for nanotheranostic reagents with excellent MRI, PA imaging, and PTT capabilities.

Materials

TMV Bioconjugation

Wild-type TMV nanoparticles were propagated in *N. benthamiana* plants and isolated from plant extracts by chloroform: butanol extraction and ultracentrifugation. The TMV concentration in plant extracts was determined using a NanoDrop 2000 UV/visible spectrophotometer (Thermo Fisher Scientific, Waltham, Mich., USA), assuming a molar extinction coefficient (ε260 nm) of about 3.0 mL mg$^{-1}$ cm$^{-1}$. The Gd-TMV nanoparticles were synthesized by carbodiimide coupling (targeting internal glutamic acid residues) to introduce alkyne ligation handles, followed by the introduction of Gd-DOTA as the MRI contrast agent.

PDA Coating

We diluted 2 mg of TMV or Gd-TMV stock solution in 20 mL Tris buffer (pH 8.5), added 2.5-7 mg dopamine to the solution dropwise while stirring, and allowed the reaction to proceed for 6 h open to the atmosphere. The product was centrifuged at 25,000 g, washed with PBS and then with deionized water. The morphology of the particles at each step was observed by transmission electron microscopy using a Tecnai F30 instrument.

Measurement of r$_1$-Relaxivity and T1-Mapping Phantoms

The Gd$^{3+}$ ionic relaxivity of the particles was tested at 37° C. using a Brukman Minispec mq60 relaxometer (60 MHz) and a BioSpec 70/30USR pre-clinical 7.0 T (300 MHz) and 9.4 T (400 MHz) MRI (Bruker Inc., Billerica, Mass., USA). NMRD profiles (1/T1) were measured at 25° C. in magnetic fields ranging in strength from 0.00024 to 0.47 T (corresponding to 0.01-20 MHz proton Larmor frequency) on a Stelar (Mede, Italy) field-cycling relaxometer, with an absolute uncertainty<1%. Data points from 0.5 T (21.5 MHz) to 1.7 T (70 MHz) were collected on a Stelar Spinmaster spectrometer. The concentration of Gd3+ was determined by inductively coupled plasma optical emission spectrometry using a 730-ES ICP-OES device (Agilent Technologies, Santa Clara, Calif., USA).

PC-3 Cell Culture

The human prostate cancer cell line PC-3 (ATCC) was maintained at 37° C. in a humidified 5% CO$_2$ atmosphere. The cells were grown in RPMI-1640 medium (Corning Life Sciences, New York, N.Y., USA) containing 10% fetal bovine serum (Atlanta Biologicals, Flowery Branch, Ga., USA) and 1% penicillin—streptomycin (Thermo Fisher Scientific).

In Vitro MRI of PC-3 Cells

Approximately 2×10$^5$ PC-3 cells were seeded per well into 24-well plates and grown overnight as above. We then added different concentrations of the nanoparticles (0, 0.1, 0.2, 0.3 and 0.4 mg mL$^{-1}$, equivalent to 0, 1×10$^6$, 2×10$^6$, 3×10$^6$ and 4×10$^6$ particles per cell, diluted in PBS) and incubated for a further 3 h. The cells were then washed three times with PBS, detached with trypsin/EDTA, transferred to Falcon tubes and embedded in 25% agarose. The in vitro MRI studies were carried out using a horizontal Biospec 7 T scanners (Bruker Inc., Billerica, Mass., USA) equipped with a 3 cm birdcage 1H coil (Bruker, Erlangen, Germany). First, a multi-slice, T2 weighted imaging sequence (RARE) 54 was used to provide location information about the cells with the following parameters: TE/TR=24/3000 ms, RARE factor=8, NAV=1, number of axial slices=15, slice thickness=1.5 mm, matrix size=128×128, 30×30 mm field of view (FOV). The total acquisition time was 48 s. Next, single-slice T1-mapping was performed using a saturation-recovery-look-locker (SRLL) sequence as previously described, and a spiral readout to accelerate acquisition. The spiral trajectory required 32 interleaves to fully sample the k-space for a FOV of 30×30 mm2 and matrix size of 128×128. The spiral SRLL used the following parameters: single slice, FA=10°, TE=3.5 ms, slice thickness=1.5 mm, NAV=1. Fifty images that covered 6 s of the saturation recovery curve were acquired at intervals of 120 ms. Proton density (MO) images were acquired with same spiral trajectory and TR=2000 ms. The spiral trajectory of 32 interleaves with 0th moment compensation was designed using the minimum-time gradient method and measured manually for reconstruction. The scan time for each average was 2 min 40 s. After imaging, the cell samples were collected and sonicated at 30% power for 30 s in ice, and the total protein content was measured using the Quick Start Bradford Protein Assay with bovine serum albumin as standard (Bio-Rad, Hercules, Calif., USA). The reset cell samples were then digested with concentrated hot HNO3 and the Gd content was determined by ICP-OES.

Photothermal Experiments

The aqueous suspension containing different concentrations of the Gd-TMV-PDA particles (1.5 mL) in a quartz cuvette was irradiated with an 808 nm laser with power settings in the range 0.38$^{-1}$ W cm$^{-2}$ for 500 s. The change in temperature was recorded using an A300 forward-looking infrared (FLIR) thermal camera (FLIR Systems, Wilsonville, Oreg., USA). The photothermal conversion efficiency of Gd-TMV-PDA was calculated using the equation η=hs (Tmax−Tsurr)−Qdis/I(1−10−Aλ), where h is the thermal conductivity index, s is the surface area of the vessel, Tmax is the equilibrium temperature during irradiation, Tsurr is the initial temperature, Qdis is the heat generated by the solvent, I is the power intensity of the laser, and Aλ is the sample's absorption value (here λ=808 nm).

Calcein-AM/PI Staining

We seeded 1×10$^5$ PC-3 cells into 10×10 mm plates and cultivated them overnight as described above. Then cells were then incubated with 500 μg mL$^{-1}$ Gd-TMV-PDA for 6 h, before washing three times in PBS to remove the excess particles. Different groups of cells were irradiated with the 808 nm laser (1 W cm$^{-2}$) for 1, 2, 3, 4, 5 or 10 min. The cells were incubated for a further 2 h then simultaneously stained for 15 min in the dark with calcein-AM and PI as part of the Live/Dead Cytotoxicity Assay Kit (MesGen Shanghai, China). The stained cells were observed on a TCS SP5 inverted microscope (Leica, Wetzlar, Germany) with a 63× oil-immersion objective lens, using 488 and 543 nm lasers to excite calcein-AM and PI, respectively.

Photoacoustic Analysis of Gd-TMV-PDA

PA imaging was performed with a multispectral optoacoustic tomography (MSOT) scanner (iThera medical, Munich, Germany), was equipped with an array of 128 cylindrically focused transducers to detect PA signals and a tunable pulsed laser (680-980 nm, 10 Hz) to generate the PA effect in polypropylene and Tygon tubes placed across the center of a water bath. The PA spectrum between 680 and 900 nm was measured with an average laser energy density of 40 mJ cm$^{-2}$. The PA behavior of Gd-TMV-PDA in aqueous solution (50, 100, 150, 200, 250 and 300 μg mL$^{-1}$,) was excited at 680 nm. The intensity was calculated by region of interest analysis on the MSOT imaging system. The PA images were reconstructed using the coherence factor-based sound speed correction method.

We have developed a nanotheranostic reagent (Gd-TMV-PDA) for dual modal imaging (MR+PA imaging) and simultaneous PTT for the treatment of cancer. The biopolymer PDA displayed on the Gd-TMV particles dramatically increased the longitudinal relaxivity, while achieving high photothermal conversion efficiency and excellent photoacoustic imaging properties. Our data showed that the Gd-TMV-PDA particles allow the localization of cancer cells by MRI and targeted killing by irradiation with an 808 nm laser in as little as 3 min.

Methods

Native and Denaturing Gel Electrophoresis

Intact native and modified TMV (10 μg per lane) were analyzed by 1% (w/v) agarose native gel electrophoresis in 0.1 M Tris-maleate running buffer (pH 6.5). Denatured protein subunits (10 μg per lane) were analyzed by polyacrylamide gel electrophoresis using 4-12% NuPAGE gels in 1×MOPS buffer (Invitrogen). Samples were denatured by boiling in SDS loading dye for 10 min. Gels were photographed under UV or white light before staining with Coomassie Brilliant Blue, and under white light after staining, using an AlphaImager system (Protein Simple, San Jose, Calif., USA).

Trypan Blue Assay

We seeded 1×10$^5$ PC-3 and 4T1 cells (ATCC) into 24-well plates and cultivated them overnight in RPMI-1640 medium (Corning Life Sciences, New York, N.Y., USA) containing 10% (v/v) fetal bovine serum (Atlanta Biologicals, Flowery Branch, Ga., USA) and 1% (w/v) penicillin—streptomycin (Thermo Fisher Scientific). The plates were assigned to one of four groups. The experimental group was PC-3 and 4T1 cells incubated with Gd-TMV-PDA (500 μg/mL) 6 h at 37° C., washed three times with PBS to remove excess particles and then irradiated with the 808-nm laser for 10 min. The three control groups were (i) PC-3 and 4T1 cells untreated, (ii) PC-3 and 4T1 cells incubated with Gd-TMV-PDA (500 μg/mL) without irradiation, and (iii) PC-3 and 4T1 cells irradiated (1 W/cm$^2$) in the absence of Gd-TMV-PDA. Following treatment, all cells were incubated at 37° C. for 2 h, stained with trypan blue for 15 min and observed under an IX71 optical microscope (Olympus, Tokyo, Japan).

Results and Discussion

Synthesis of Gd-TMV-PDA and Characterization

TMV nanoparticles were propagated in and isolated from *Nicotiana benthamiana* plants, which are inexpensive to grow and highly scalable. The high-resolution crystal structure of TMV (FIG. 1A1) includes an internal glutamic acid residue (GLU97/106, blue) and an external tyrosine residue (TYR139, red) that can be functionalized using the well-established copper-catalyzed azide-alkyne cycloaddition (CuAAC) strategy, also known as click chemistry. The internal TMV surface was modified with alkyne groups then conjugated with the macrocyclic T1-MRI contrast agent Gd-DOTA-azide via a click reaction.

Both native TMV and Gd-TMV (2 mg) were coated with PDA by in situ self-polymerization with dopamine under the same conditions, varying the dopamine dose in the range 2.5-7 mg. The morphology of the particles after each modification step was observed by transmission electron microscopy (TEM). The native TMV nanoparticles showed the typical elongated nanostructure (FIG. 1B1) and a clean, smooth external surface (FIG. 1B2). After internal chemical conjugation with Gd-DOTA, the Gd-TMV particles (FIGS. 1E1 and 2) retained the shape and morphology of the native TMV particles. When the native TMV particles (2 mg) were coated with PDA using 2.5 mg dopamine, the particles were homogenously coated but remained discrete (FIGS. 1C1 and 2). In contrast, at the higher dose of 3.5 mg dopamine, the PDA coat was thicker and longer with thorn-like protuberances, and the particles tended to aggregate (FIGS. 1D1 and 2). Interestingly, increasing the dopamine dose from 2.5 to 7 mg caused significant changes to the PDA coating on the Gd-TMV particle surface, with knot-like protrusions 10-40 nm in depth forming at dopamine doses of 2.5 (FIG. 1F), 3.5 (FIG. 1G), and 5 mg (FIG. 1H), but both a full coating and knots at the highest dose of 7 mg (FIG. 1I). Generally, the knot-like PDA deposits preferentially formed on the ends of the particles but more appeared on the body as the dopamine dose increased. Similar results were reported previously for the PDA-coated TMV used to grow gold nanoparticles under acidic conditions. We concluded that Gd-TMV-PDA particles with a consistent morphology could be prepared using 2.5-3.5 mg dopamine, and we used the Gd-TMV-PDA sample prepared with 3.5 mg dopamine for all further characterizations and applications.

Longitudinal Relaxivity of Gd-TMV-PDA and MRI of Cancer Cells

Figure 2B:
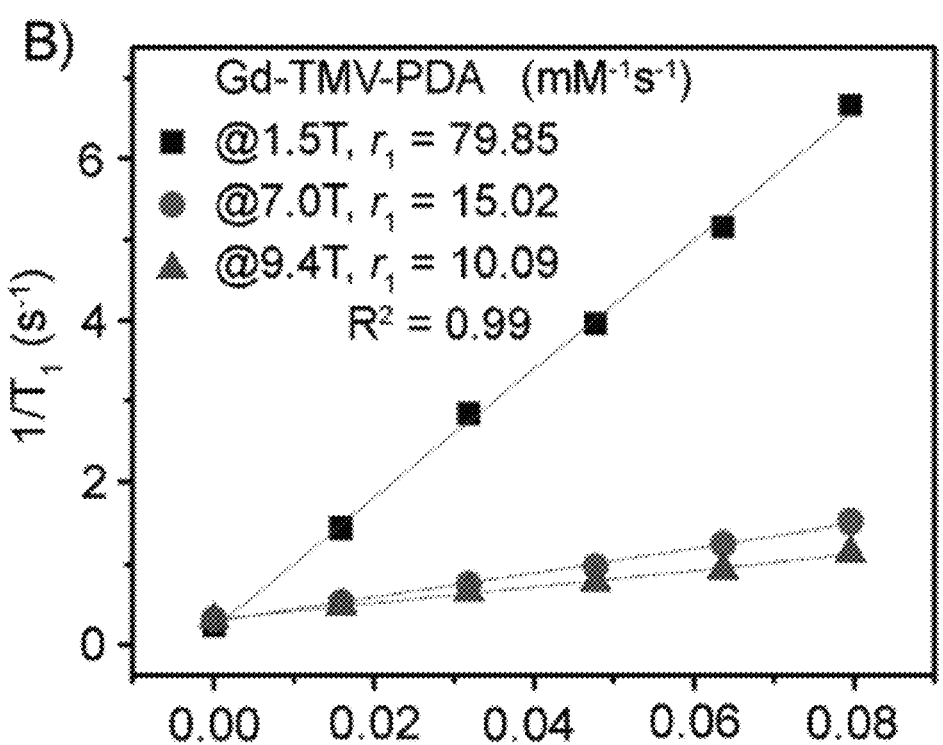

The longitudinal relaxivity (r1) of the Gd-TMV-PDA nanoparticles was measured in different magnetic fields (1.5, 7.0 and 9.4 T) as shown in FIGS. 2A and B. The $r_1$ values of the Gd-TMV particles (per Gd3+) were 13.63, 5.75 and 5.25 mM$^{-1}$ s$^{-1}$ at 1.5, 7 and 9.4 T, respectively (FIG. 2A), corresponding to per particle values of ~20 613, 8696 and 7940 mM$^{-1}$ s$^{-1}$ at 1.5, 7 and 9.4 T, respectively. The $r_1$ values of the Gd-TMV particles agreed with previous reports describing these contrast agents and were higher than the values of commercial T1 MRI contrast agents (3$^{-5}$ mM$^{-1}$ s-). Interestingly, after PDA coating, the r1 values dramatically increased to 79.85, 15.02 and 10.09 mM$^{-1}$ s$^{-1}$ (per Gd$^3$±) at 1.5, 7.0 and 9.4 T, respectively, corresponding to per particle values of ~120,757, 22,715 and 15,260 mM$^{-1}$ s$^{-1}$ at 1.5, 7.0 and 9.4 T, respectively (FIG. 2B). Gd-TMV-PDA particles therefore appear to achieve among the highest r$_1$ values compared to either analogue protein-based nanostructures or inorganic nanoparticles under similar conditions. For example, the longitudinal relaxivity values of our Gd-TMV-PDA particles were ~4-fold higher than Gd-P22 (21.7 mM$^{-1}$ s$^{-1}$) at 28 MHz almost ~5-fold higher than Gd-MS2 (16.9 mM$^{-1}$ s$^{-1}$) and Gd-CPMV (15.5 mM$^{-1}$ s$^{-1}$) at ~64 MHz, ~2.5-fold higher than Gd-MS2 in ultra-high-strength magnetic fields (4.3 mM$^{-1}$ s$^{-1}$ at 9.4 T), and ~3-fold higher than mesoporous silica and polymer nanoparticles. The longitudinal relaxivities of these functionalized nanoparticles are compared in the following Table.

TABLE

The longitudinal relaxivities of Gd-conjugated nanoparticles described in the literature compared to our new Gd-TMV-PDA formulation

| Compounds | size (nm) | $r_1$ (mM$^{-1}$ s$^{-1}$) | field (MHz) |
|---|---|---|---|
| Gd(DOTA)-TMV-PDA | 18 × 300 | 15.02/79.85 | 300/60 |
| Gd(DTPA)-MS2 | 27.4 | 4.3/16.9 | 400/60 |
| Gd(DOTA)-AaLS | 15 | 16.49/30.24 | 300/60 |
| Gd(DOTA)-TMV | 18 × 300 | 14.6 | 60 |
| Gd(DOTA)-CPMV | 28 | 11.9-15.5 | 64 |
| Gd(DTPA)-P22 | 64 | 21.7 | 28 |
| GdAAZTA-Dendrimer | 25 kDa | 31.4 | 60 |
| Gd(DOTAGA)-MSN | 30 | 28/37 | 60/20 |
| Gd(DOTAGA)-MSN | 25-220 | 20.3-79.1 | 20 |
| Gd(DOTA)-Dendrimer | 142 | 22.4 | 60 |
| Gd(DOTA)-PLGA | 150-170 | 17.5 | 60 |
| Gd(DOTA)-PLGA | 140 | 21.7 | 21.5 |
| Gd(DTPA)-PLNP | 109 | 6.72 | 50 |
| Gd(HPDO3A)-PN | | 17 | 60 |
| Gd(DTPA)DNA-Au | 30 | 20 | 60 |
| Gd(DOTA)-MSN | 20-50 | 26.6 | 20 |
| Gd(DTPA)-MSNR | 107-535 | 22 | 20 |

Figure 6:
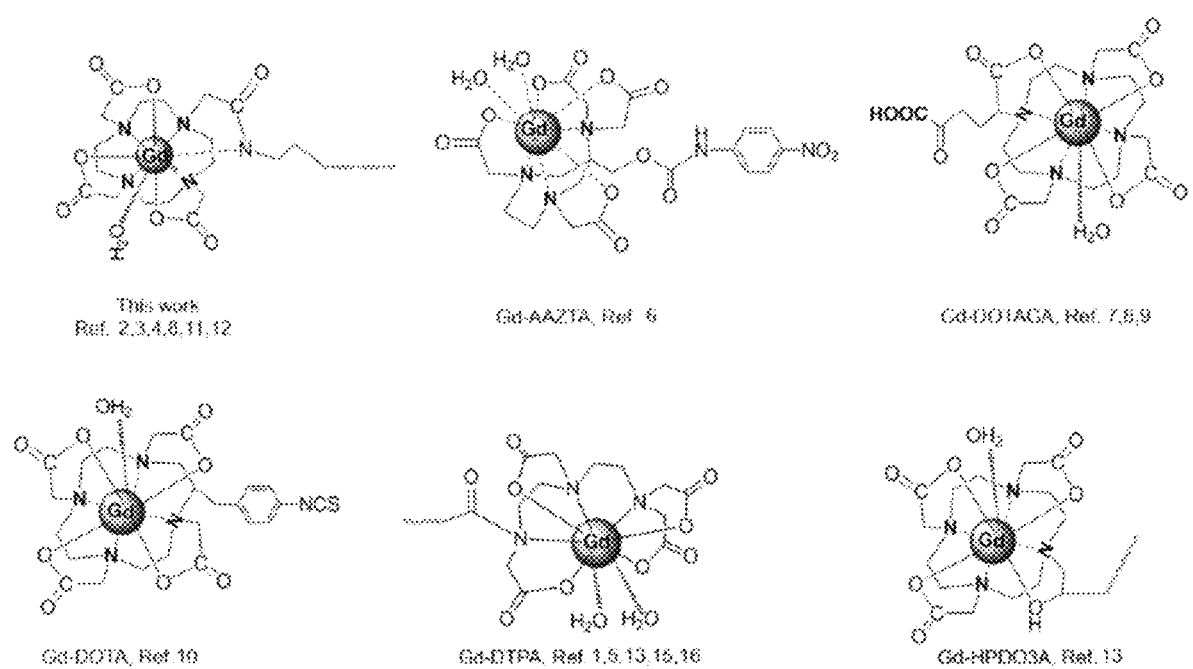
FIG. 6 illustrates the molecular structure of the macrocyclic Gd complex upon which we based our MRI agent.

AaLS: *Aquifex aeolicus*, AAZTA: 6-amino-6-methylperhydro-1,4-diazepine tetraacetic acid, TMV: Tobacco mosaic virus, CPMV: Cowpea mosaic virus, PLNP: persistent luminescent nanoparticles; PN: peptide nanofiber; MSN: mesoporous silica nanoparticles; PLGA: poly(D,L-lactide-co-glycolide). The molecular structures of the Gd- complex are shown in FIG. 6.

Figure 2C:
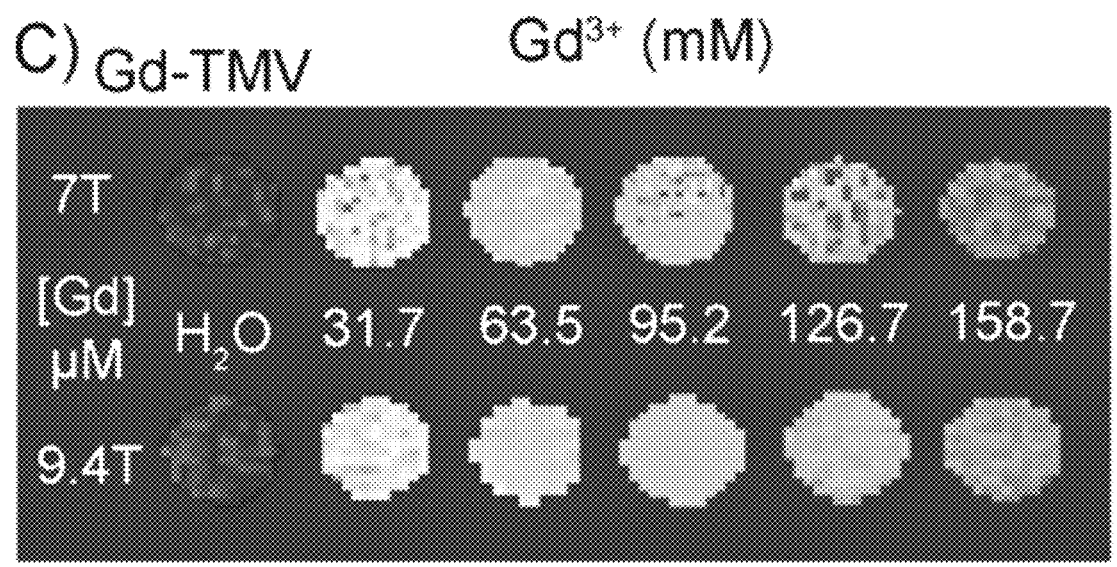
Figure 2D:
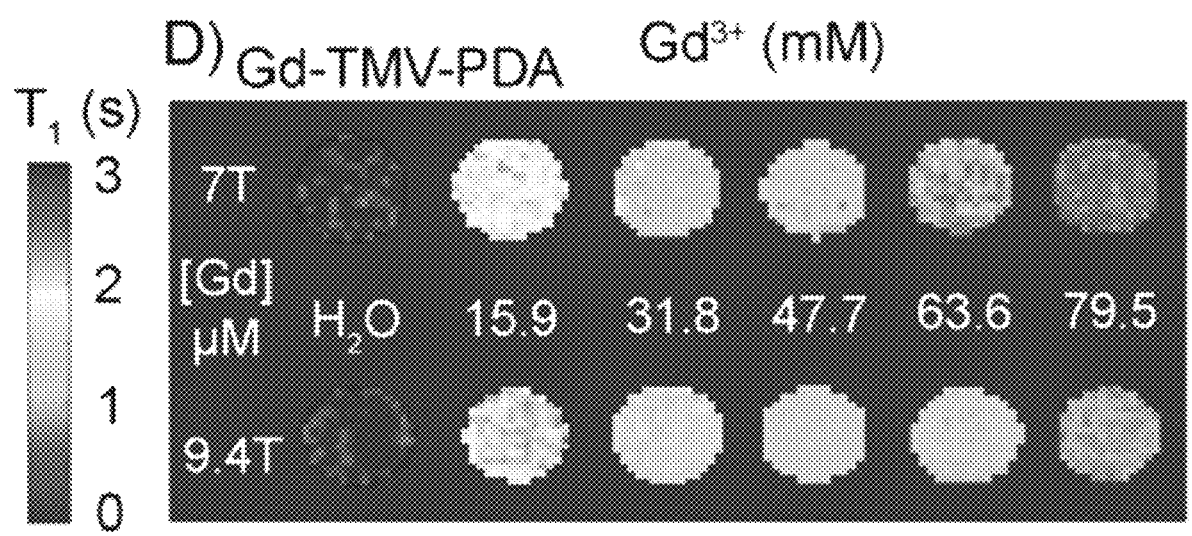

To demonstrate the suitability of the new contrast agents for ultra-high-field MRI (UHFMRI), we obtained concentration dependent T1-mapping phantom images of the Gd-TMV-PDA water solutions at 7.0 and 9.4 T (FIG. 2D), and compared them to the Gd-TMV phantoms (FIG. 2C). The T1-mapping images of Gd-TMV-PDA showed a clear Gd$^{3+}$ concentration-dependent positive contrast gradient from 0 to 79.5 μM (158.7 μM in Gd-TMV). Gd-TMV-PDA therefore achieved higher contrast efficiency than Gd-TMV but only required 50% of the Gd$^{3+}$ concentration in each phantom compared to Gd-TMV.

Figure 2E:
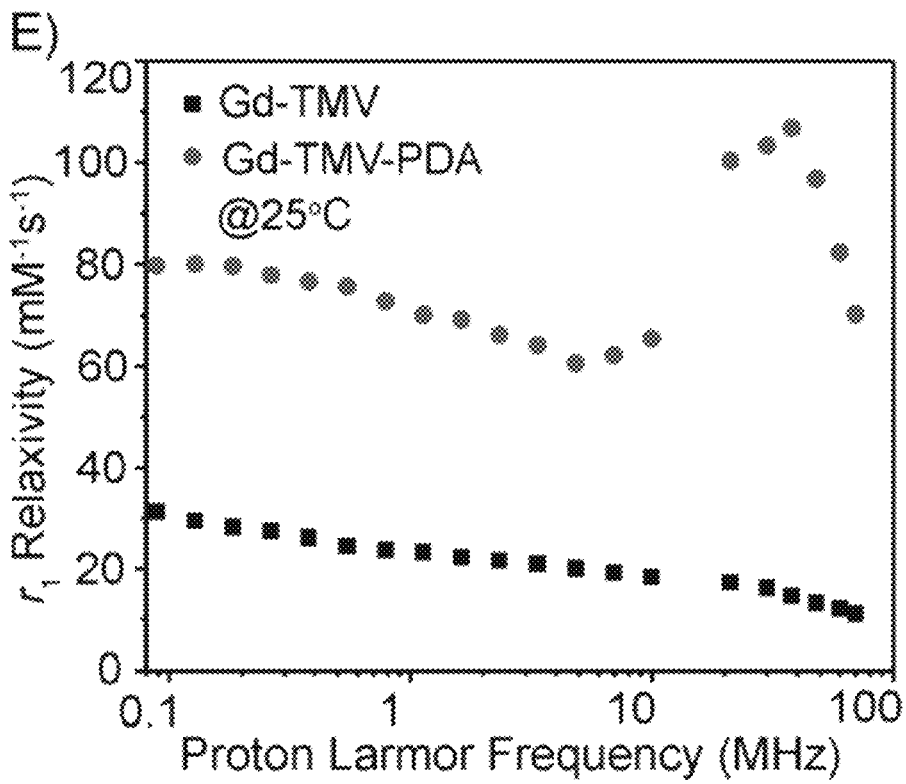

An increase in the relaxivity of Gd-based contrast agents can be achieved by optimizing the exchange rate τM (in the order of nanoseconds) for the metal-coordinated water molecules, and the rotational correlation times (τR) for the metal complex. Such strategies can be realized by immobilizing the Gd-complex on nanostructured materials, slowing down their molecular tumbling while maintaining the water residence time. We therefore carried out a thorough relaxometric characterization of the Gd-TMV-PDA particles by measuring the nuclear magnetic relaxation dispersion (NMRD) profiles of Gd-TMV and Gd-TMV-PDA over the frequency range 0.1-70 MHz at 25° C. (FIG. 2E). The NMRD profiles were identical, with a relaxivity peak centered on 40 MHz indicating slowly tumbling systems. Therefore, the dramatically increased longitudinal relaxivity of Gd-TMV-PDA compared to Gd-TMV could reflect two major factors. First, the PDA coating may increase the rigidity of the Gd-DOTA complex, increasing the τR value. Alternatively, given that water molecules inside carbon nanotubes experience extremely high flow velocities, PDA with its abundant hydroxyl groups may present more hydrophilic residues to bind water molecules with access to Gd-DOTA resulting in faster exchange between Gd-coordinated internal water and bulk water. Notably, the relaxivity peak of most T1 contrast agents centers on ~21 MHz, and the greater peak shift revealed by our particles in higher strength magnetic fields confirms their suitability for UHFMRI.

Figure 2F:
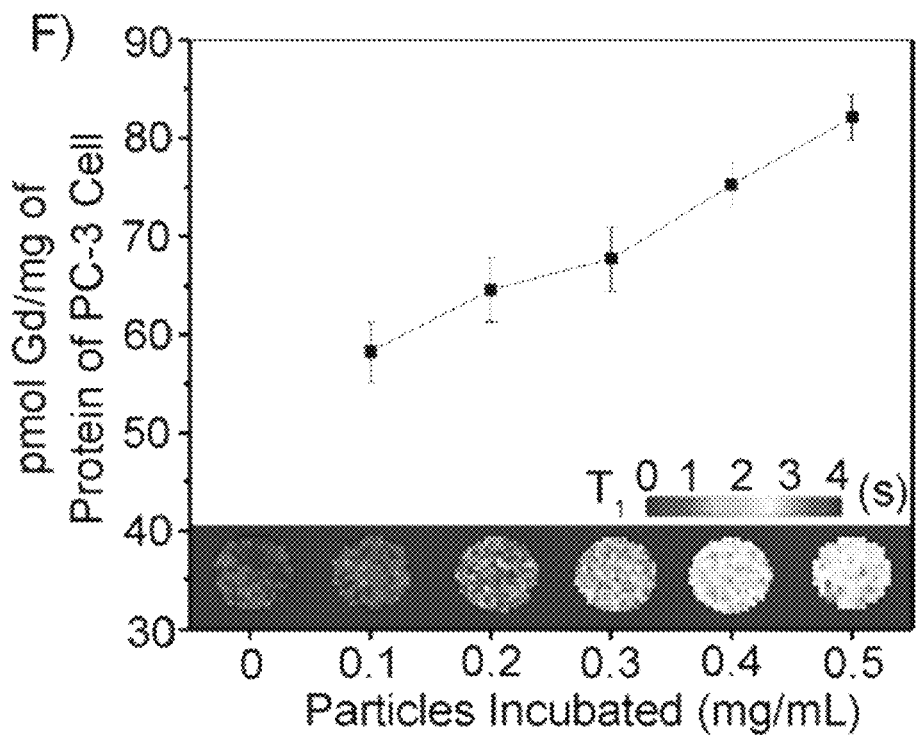

Finally, to evaluate the ability of the particles to detect cancer cells by UHFMRI, the prostate cancer cell line PC-3 was incubated for 3 h at 37° C. with different concentrations of Gd-TMV-PDA (0.1, 0.2, 0.3 0.4 and 0.5 mg mL-1) and then the cells were immobilized in agarose. A T1-mapping MRI scan revealed that the nanoparticles reduced the normalized T1 value in a concentration-dependent manner (FIG. 2F). The quantity of Gd$^{3+}$ taken up by PC-3 cells per mg protein was determined by ICP-OES and the Bradford protein assay, revealing a concentration-dependent range of 58.3-82.1 pmol Gd$^{3+}$ per mg protein for the Gd-TMV-PDA nanoparticles. These particles were passively taken up by cancer cells in a relatively efficient manner, consistent with earlier reports showing that elongated nanoparticles can pass through cell membranes more effectively than spherical nanoparticles due to their high degree of nanoparticle-to-cell contacts.

PTT Properties of Gd-TMV-PDA and Cancer Cell Killing Profiles

Figure 8C:
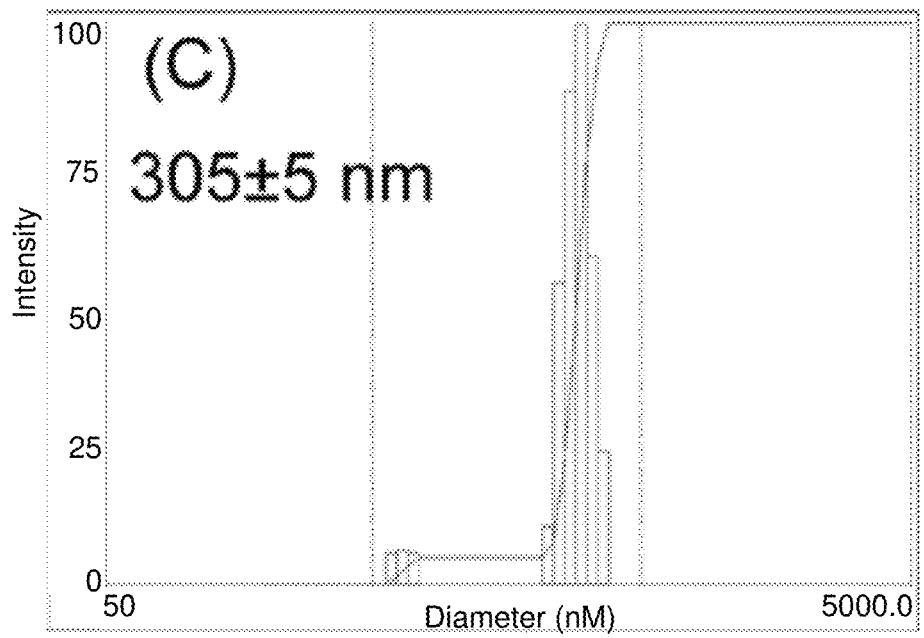
FIGS. 8(A-D) illustrate transmission electron micrographs of Gd-TMA-PDA (A) before and (B) after 808 nm laser (1 W/cm2) irradiation for 10 min, and the corresponding dynamic light scattering (DLS) of the sample samples (C) before and (D) after irradiation. There were no obvious changes in the morphology and size of the Gd-TMA-PDA particles (A, C) before and (B, D) after 808-nm laser irradiation for 10 min at a power density of 1 W/cm2 confirming the photothermal stability of the particles.
Figure 8D:
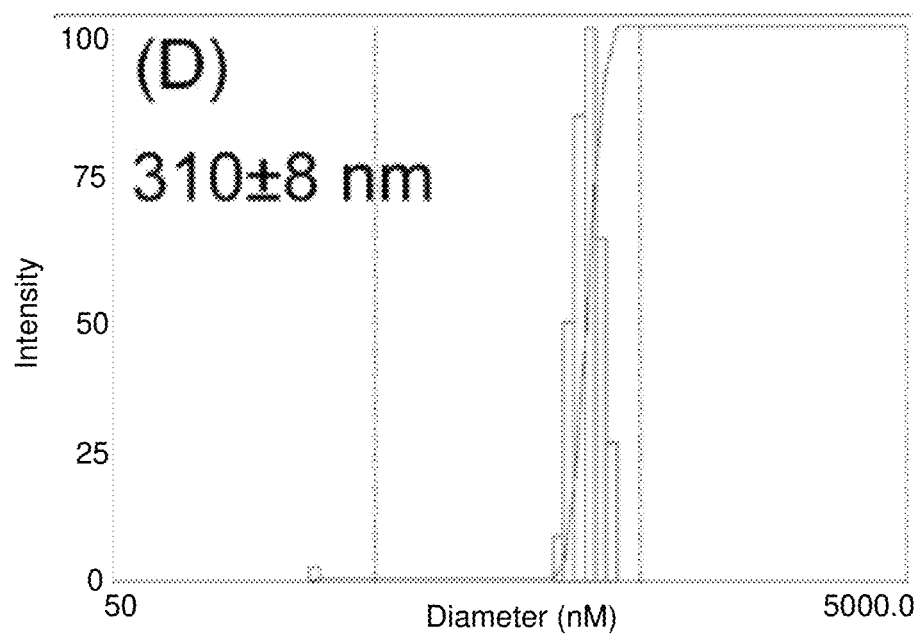

Next, we investigated the photothermal properties and in vitro cytotoxicity of the Gd-TMV-PDA particles (FIG. 3). The particles exhibited a broad absorption range (600-1000 nm) as shown by the absorption spectra (FIG. 3A). The absorbance at 808 nm was linearly correlated with the concentration of the particles (FIG. 7). The heat generated by different concentrations of Gd-TMV-PDA (50, 100, 200, 400, 500 and 667 μg mL$^{-1}$) was monitored using a near-infrared (NIR) camera to record the temperature profile in response to irradiation with an 808 nm NIR laser (1 W cm$^{-2}$) for 5 min (FIG. 3B). The Gd-TMV-PDA solution underwent rapid heating during irradiation, with the temperature rise dependent on the particle concentration and the duration of the laser pulse, indicating that heat generation can be finely tuned. After 5 min, the temperature of the 50, 100, 200, 400, 500 and 667 μg m$^{-1}$ Gd-TMV-PD solutions increased from room temperature (25° C.) to 28.8, 30.6, 33.4, 37.8, 40.4 and 44.1° C., respectively. The PBS control solution did not increase in temperature when exposed to the same stimulus. We also investigated the thermal effect of a 667 μg mL$^{-1}$ Gd-TMV-PD solution irradiated with the 808 nm laser at different power densities ranging from 0.4 to 1 W cm$^{-2}$ (FIG. 3C). The change in temperature ranged from 7.4 to 19.1° C. depending on the laser power. Based on these data, the photothermal conversion efficiency of the Gd-TMV-PDA particles was calculated, yielding a value of 28.9%. This is similar to the efficiency of widely-used photothermal agents such as Fe@Fe$_3$O$_4$ (24.4%), gold nanocages (13%), gold nanorods (21%), and Cu$_{2-x}$Se (22%). To confirm the stability of the Gd-TMV-PDA particles after laser irradiation, we observed the morphology by TEM, tracked the particles size by dynamic light scattering (DLS) (FIG. 8) and monitored the absorption spectra of the Gd-TMV-PDA solution after before and after irradiation (FIG. 3A). There were no obvious differences in absorption or particle morphology, indicating that the particles are photothermally stable. The stock solution of 200 μg mL$^{-1}$ Gd-TMV-PDA remained homogeneous after irradiation (FIG. 3A, inset). Moreover, after eight cycles of laser irradiation, the laser-induced temperature increases in the solution were unchanged (FIG. 3E). In contrast, gold nanorods change into cross-linked nanowires following laser irradiation, causing the absorption peak in the NIR region (and the red color) to disappear, and a gradual decline in the temperature increase during irradiation. These data show that Gd-TMV-PDA particles benefit from both high photothermal conversion efficiency and high photothermal stability.

Figure 3A:
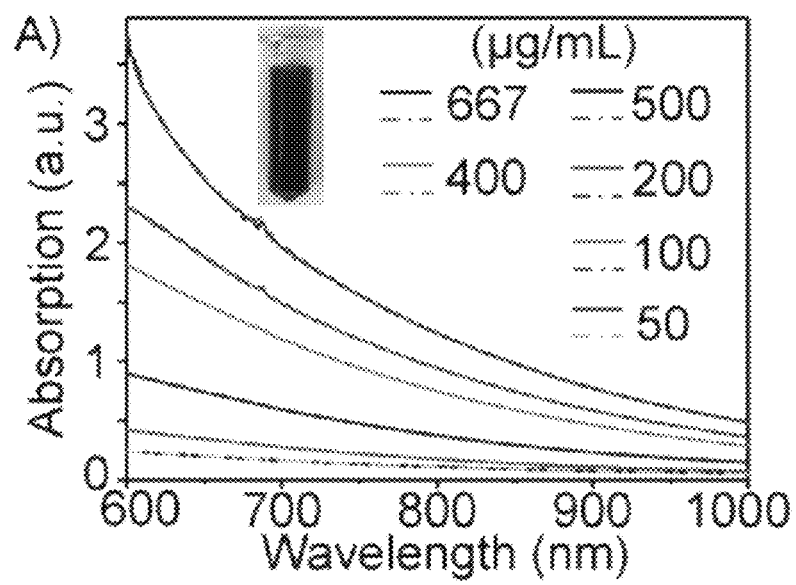
FIGS. 3(A-F) illustrate (A) Absorption spectra of Gd-TMV-PDA at different concentrations before (solid line) and after (dashed line) irradiation (808 nm laser, 1 W $cm^{-2}$). Inset shows a picture of the 200 μg $mL^{-1}$ Gd-TMV-PDA solution. (B) Thermal images of different concentrations (50-667 μg $mL^{-1}$) of Gd-TMV-PDA irradiated for different durations (808 nm laser, 1 W $cm^{-2}$) recorded with an IR camera, and (C) the corresponding temperature change profiles. (D) Temperature profiles and thermal images of 667 μg $mL^{-1}$ Gd-TMV-PDA solution irradiated with an 808 nm laser at different power densities. ($0.4^{-1}$ W $cm^{-2}$). (E) Temperature variations of a Gd-TMV-PDA over eight cycles of heating and natural cooling. (F) Confocal fluorescence images of live (calcein-AM)/dead (propidium iodide) PC-3 cells treated with Gd-TMV-PDA before and after irradiation (808 nm laser, 1 W $cm^{-2}$) for different durations (1-5 min). Scale bar=50 μm.
Figure 3B:
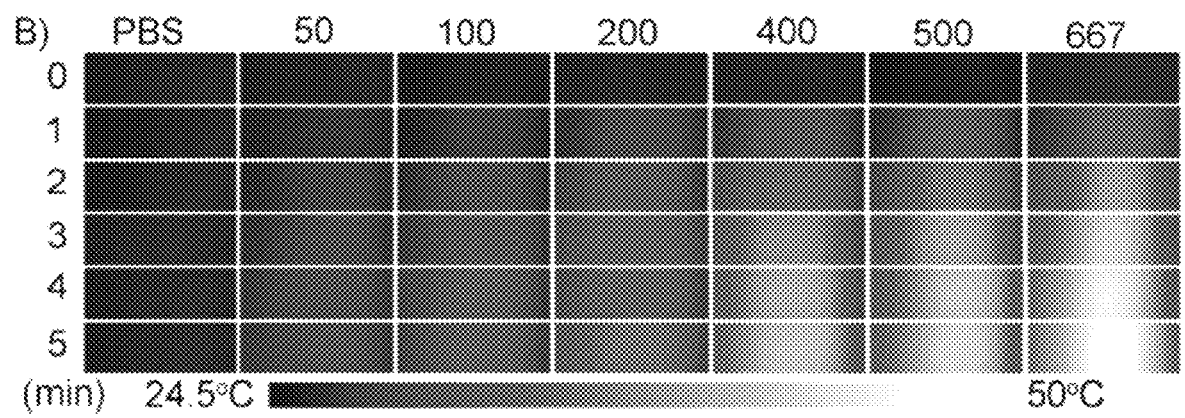
Figure 3C:
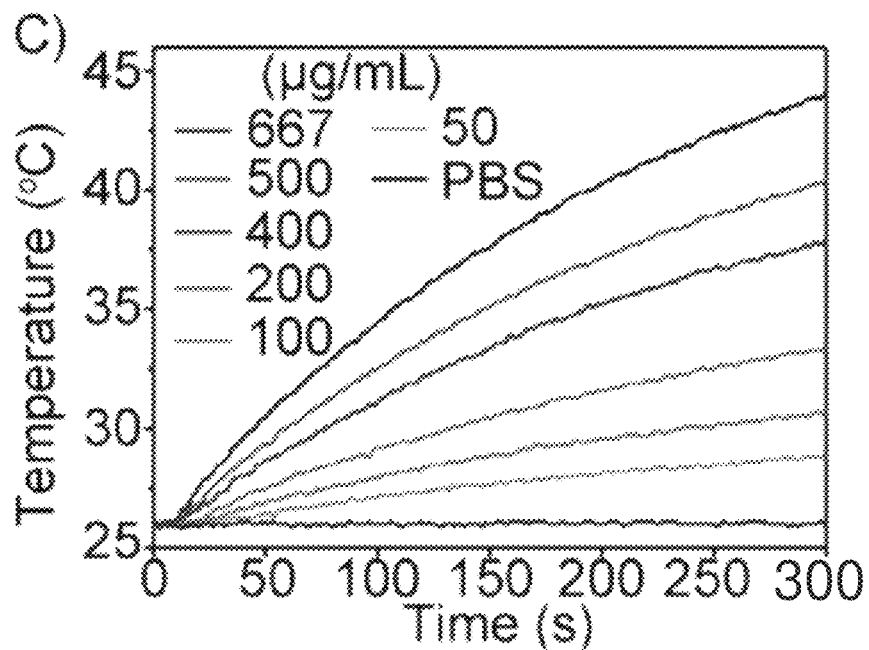
Figure 3D:
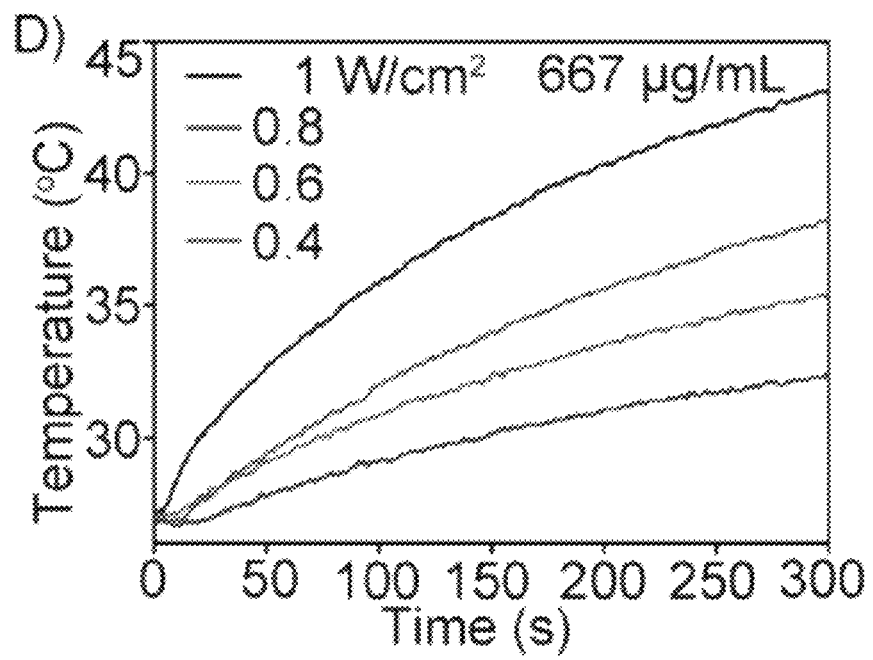
Figure 3E:
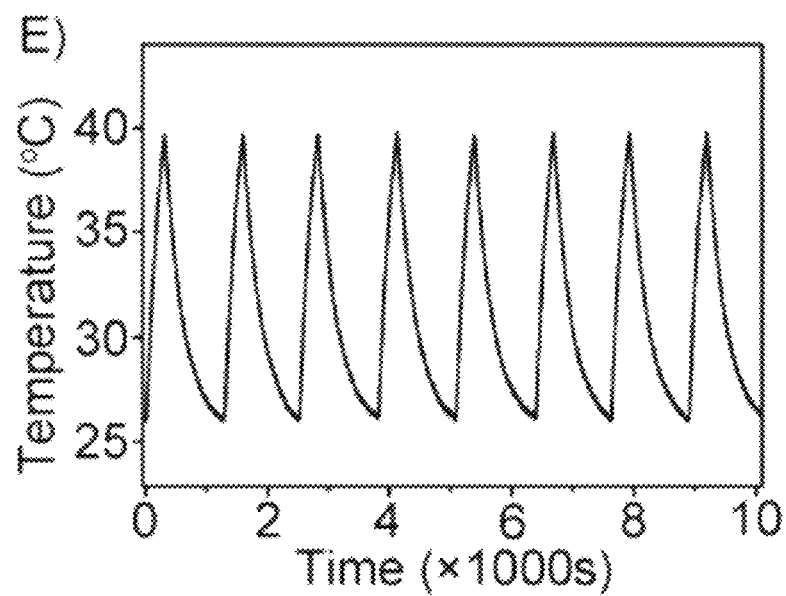
Figure 3F:
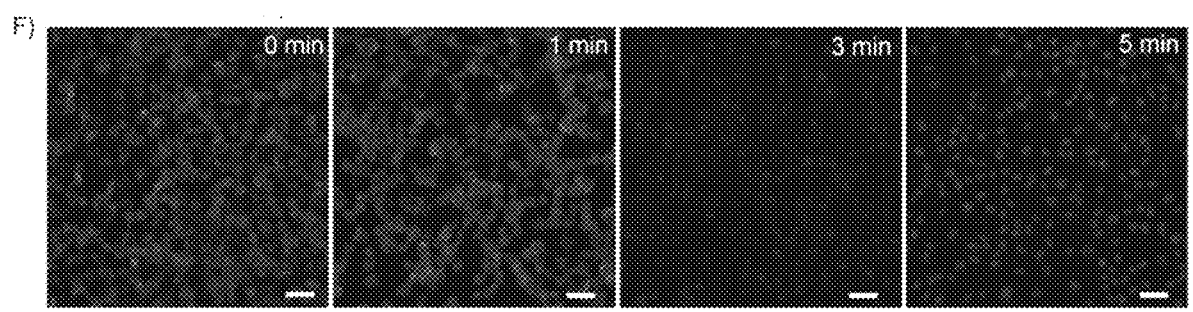
Figure 9:
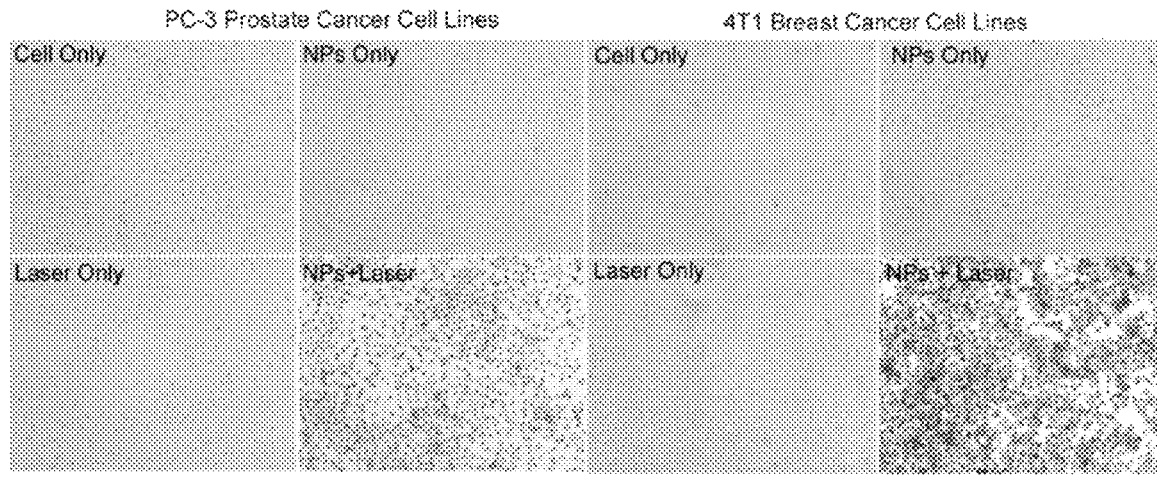
FIG. 9 illustrates trypan blue staining assay of PC-3 and 4T1 cancer cell treated with Gd-TMV PDA. The experimental group (NPs±laser) was PC-3 and 4T1 cells incubated with Gd-TMV-PDA (500 μg/mL) 6 h at 37° C. washed three times with PBS to remove excess particles and then irradiated with the 808-nm laser for 10 min. Nearly all these cells stained blue, indicating the ablation of cancer cells by the photothermal effect of Gd-TMV-PDA. The three control groups were PC-3 and 4T1 cells untreated (cells only), PC-3 and 4T1 cells incubated with Gd-TMV-PDA (500 μg/mL) without irradiation (NPs only), PC-3 and 4T1 cells irradiated. (1 W/$cm^1$) in the absence of Gd-TMV-PDA (laser only). Most of the control groups cells remained viable and did not take up the blue stain, therefore indicating neither the particle or laser did induce the death of cell lines. Both of the cell lines found significance death after incubated with Gd-TMV-PDA under laser irradiation that means the photothermal effect of the Gd-TMV-PDA particles killed the cell efficiently.
Figure 10:
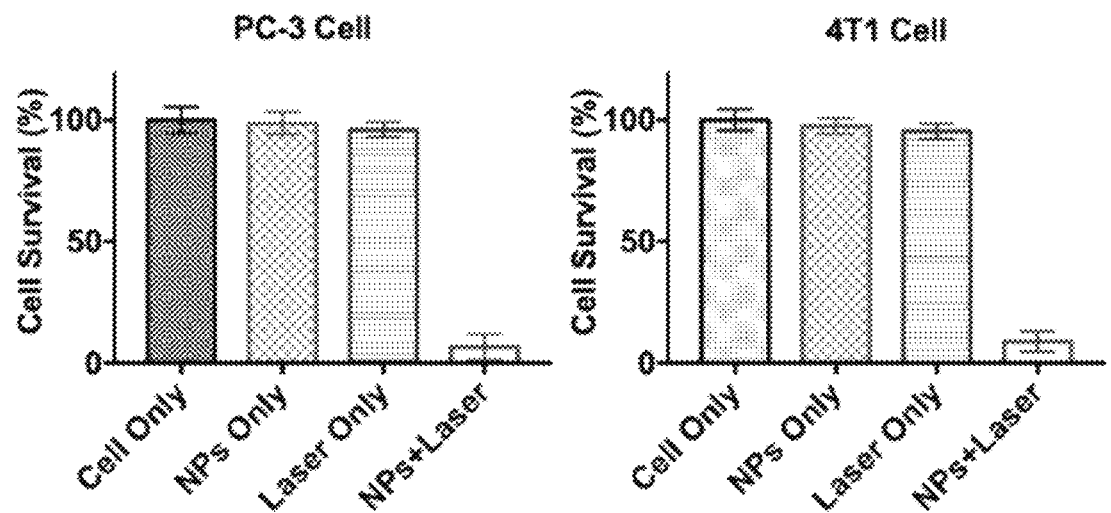
FIG. 10 illustrates MTT cytotoxicity assay of PC-3 and 4T1 cells untreated (cells only), incubated with Gd-TMV-PDA (500 μg/mL) without irradiation (NPs only), irradiated under 808 nm laser W/$cm^2$) without Gd-TMV-PDA (laser Only), and irradiated under 808 nm laser (1 W/$cm^2$) with incubated with Gd-TMV-PDA (NPs laser, experimental group) 6 hours at 37° C.

To confirm that Gd-TMV-PDA particles can be used as photothermal agents to kill cancer cells, we conducted a fluorescence-based live/dead cell assay and directly visualized the cytotoxicity of Gd-TMV-PDA particles towards human PC-3 prostate cancer cells by confocal laser scanning microscopy (CLSM). Following laser irradiation (808 nm, 1 W cm$^{-2}$), the PC-3 cells were simultaneously stained with calcein-AM and propidium iodide (PI) to distinguish live cells (green fluorescence) from dead ones (red fluorescence). As shown in FIG. 3F, the proportion of dead PC-3 cells was dependent on the duration of laser irradiation. Compared with the cells that were not irradiated, significant red fluorescence was observed 3 min after irradiation, and the tumor cells were killed completely within 5 min. The photothermal ablation efficacy of Gd-TMV-PDA was confirmed by trypan blue staining and cytotoxicity MTT assays (FIG. 9). In the three control groups (PC-3 cells alone, PC-3 cells cultured with Gd-TMV-PDA (500 μg mL$^{-1}$) without irradiation, and PC-3 cells irradiated (1 W cm$^{-2}$ in the absence of Gd-TMV-PDA), we observed hardly any dead cells. However, nearly all the PC-3 cells incubated with Gd-TMV-PDA and exposed to the laser were stained blue, indicating the ablation of cancer cells consistent with the results of the calcein-AM/PI assay. Therefore, both assays confirmed the powerful thermal cytotoxicity of Gd-TMV-PDA towards cancer cells. We also confirmed PTT efficacy using the 4T1 cell line derived from mice and serving as a model for aggressive breast cancer which showed similar results as PC-3 (FIG. 9).

PA Properties of Gd-TMV-PDA

Figure 4A:
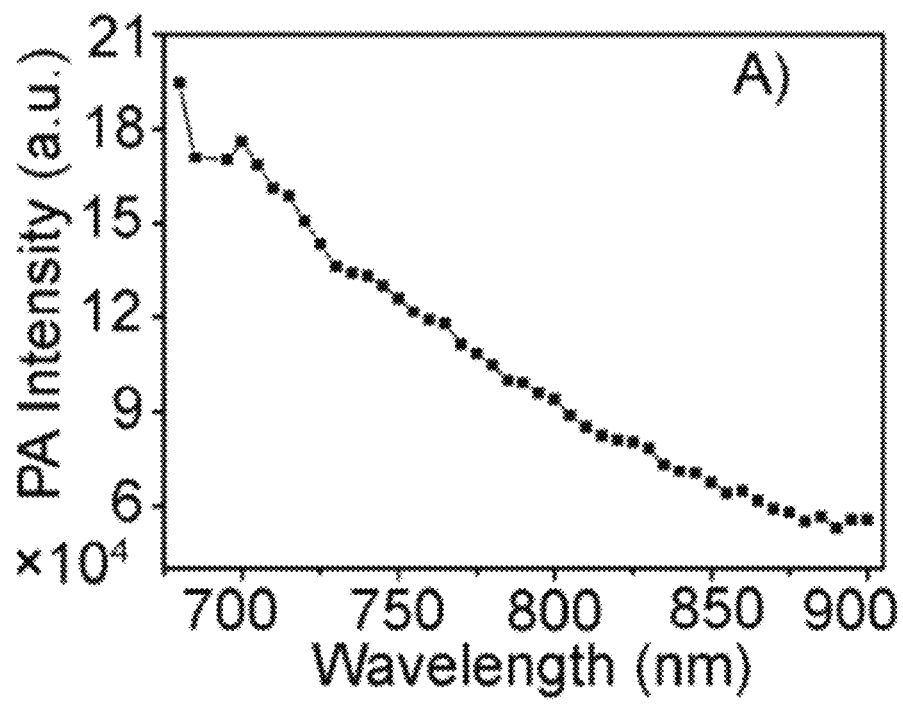
FIGS. 4(A-B) illustrate graphs and imaging phantoms showing: (A) The photoacoustic (PA) spectrum of Gd-TMV-PDA (200 μg $mL^{-1}$ aqueous solution) scanned over the wavelength range 680-900 nm; and (B) PA imaging phantoms and corresponding liner relationship between the PA signal intensity and concentration of Gd-TMV-PDA irradiated using a 680 nm pulsed laser.
Figure 4B:
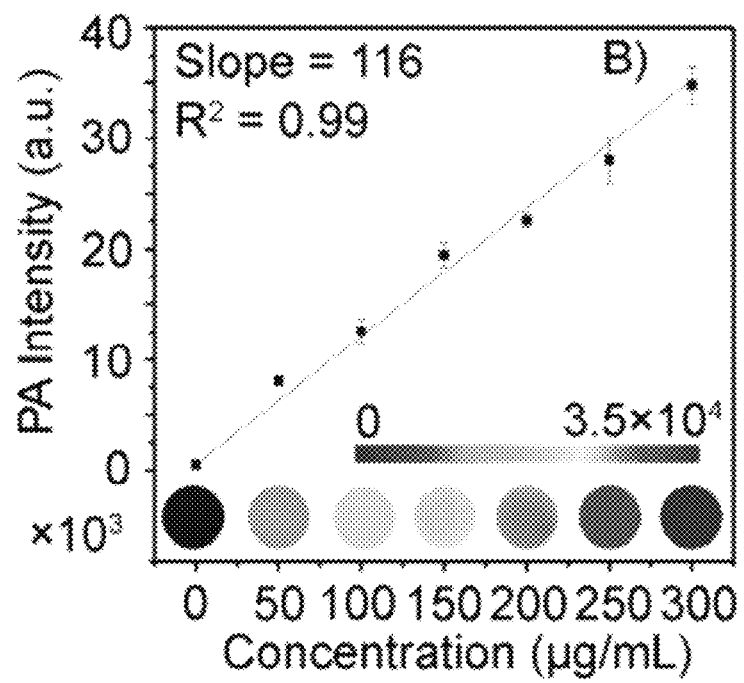
Figure 5:
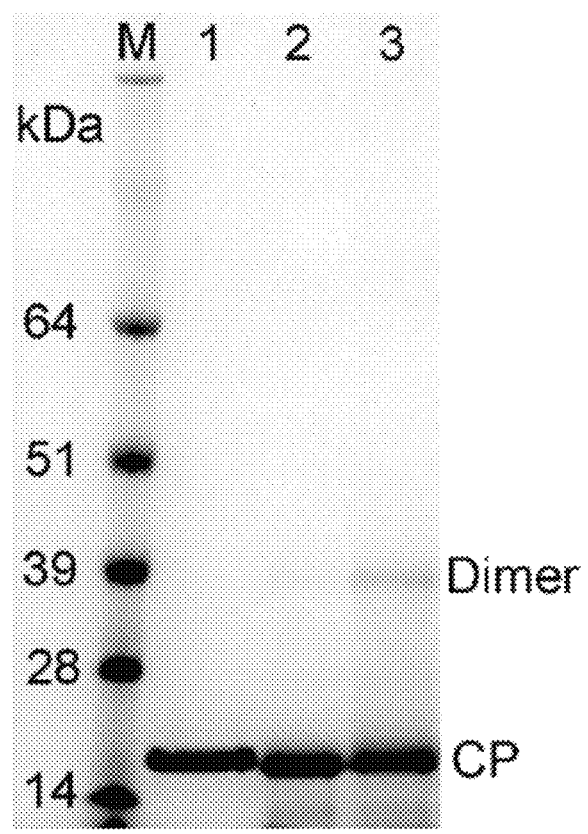
FIG. 5 illustrates sodium dodecylsulfate polyacrylamide gel electrophoresis (SDS-PAGE) for the analysis of (1) native TMV, (2) Gd-TMV, (3) Gd-TMV-PDA; CP=coat protein.

Given the excellent photothermal properties of the Gd-TMV-PDA particles, next we investigated its PA characteristics because photothermal and PA behaviors are always associated. A solution of Gd-TMV-PDA particles (200 μg mL$^{-1}$, aqueous solution) emitted clear PA signals following irradiation with a pulsed laser in the wavelength range 680-900 nm (FIG. 4A). Stronger signals were produced at shorter incident wavelengths, which is consistent with the absorption properties of Gd-TMV-PDA (FIG. 3A). The PA imaging phantoms of several concentrations of Gd-TMV-PDA (50-300 μg mL$^{-1}$) in PBS were scanned, yielding clear and homogenous images with a linear relationship between the signal and the concentration of Gd-TMV-PDA (FIG. 4B).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A nanoparticle comprising:
 a rod-shaped plant virus like particle (VLP), one or more gadolinium contrast agents conjugated to an interior surface of the VLP, and a layer of polydopamine (PDA) coated over a portion of the exterior surface of the VLP, wherein the nanoparticle PDA layer is prepared by in situ self-polymerization of dopamine.

2. The nanoparticle of claim 1, wherein the rod-shaped virus belongs to the Virgaviridae family.

3. The nanoparticle of claim 2, wherein the rod-shaped virus is a tobacco mosaic virus (TMV).

4. The nanoparticle of claim 1, wherein the weight ratio of the VLP conjugated with the gadolinium contrast agents to polydopamine is about 1:1 to about 1:2.

5. The nanoparticle of claim 1, wherein the gadolinium contrast agent is a chelated gadolinium $T_1$ contrast agent.

6. The nanoparticle of claim 5, wherein the chelated gadolinium $T_1$ contrast agent is gadolinium-DOTA (Gd-DOTA).

7. The nanoparticle of claim 1, wherein the one or more gadolinium contrast agents are directly conjugated to the rod-shaped plant VLP.

8. The nanoparticle of claim 1, wherein the one or more gadolinium $T_1$ contrast agents are conjugated to the rod-shaped plant VLP via a linker.

9. A method of detecting and/or treating cancer in a subject in need thereof, comprising:
 administering to the subject a plurality of nanoparticles, the nanoparticles including rod-shaped plant virus like particles (VLPs), one or more gadolinium contrast agents conjugated to interior surfaces of the respective VLPs, and layers of polydopamine (PDA) coated over a portion of the exterior surfaces of the respective VLP, wherein the nanoparticle PDA layers are prepared by in situ self-polymerization of dopamine;
 detecting the nanoparticles in the subject using one or more imaging devices subsequent to administering the nanoparticles to determine the location and/or distribution of the cancer in the subject; and optionally
 delivering photothermal therapy (PTT) to the VLPs in the determined location of the cancer in the subject.

10. The method of claim 9, wherein the rod-shaped virus belongs to the Virgaviridae family.

11. The method of claim 10, wherein the rod-shaped virus is a tobacco mosaic virus (TMV).

12. The method of claim 9, wherein the weight ratio of the VLP conjugated with the gadolinium contrast agents to polydopamine is about 1:1 to about 1:2.

13. The method of claim 9, wherein the gadolinium contrast agent is a chelated gadolinium $T_1$ contrast agent.

14. The method of claim 13, wherein the chelated gadolinium $T_1$ contrast agent is gadolinium-DOTA (Gd-DOTA).

15. The method of claim 9, wherein the one or more gadolinium contrast agents are directly conjugated to the rod-shaped plant VLP.

16. The method of claim 9, wherein the cancer is selected from breast cancer and prostate cancer.

17. The method of claim 9, wherein the one or more imaging devices are selected from the group consisting of a magnetic resonance imagery (MRI) modality and a photoacoustic (PA) imaging modality.

18. The method of claim 9, wherein PTT comprises the use of a device that emits electromagnetic radiation such that at least a portion of cancer cells in the detected cancer are damaged or killed.

* * * * *

UNITED STATES PATENT AND TRADEMARK OFFICE
CERTIFICATE OF CORRECTION

| | | |
|---|---|---|
| PATENT NO. | : 11,529,430 B2 | Page 1 of 1 |
| APPLICATION NO. | : 17/129490 | |
| DATED | : December 20, 2022 | |
| INVENTOR(S) | : Steinmetz et al. | |

It is certified that error appears in the above-identified patent and that said Letters Patent is hereby corrected as shown below:

On the Title Page

Item (12), should read: Steinmetz et al.

Item (72) Inventors:
Add the following inventor --He Hu, Cleveland, OH (US)--

Signed and Sealed this
Twelfth Day of November, 2024

Katherine Kelly Vidal
*Director of the United States Patent and Trademark Office*